United States Patent
Garceau et al.

(10) Patent No.: US 10,111,883 B1
(45) Date of Patent: Oct. 30, 2018

(54) SELECTIVE P2X3 MODULATORS

(71) Applicants: BELLUS Health inc., Laval (CA); Neomed Institute, Montreal (CA)

(72) Inventors: Denis Garceau, Laval (CA); Antonios Matzouranis, Laval (CA); Roberto Bellini, Laval (CA); Kemal Payza, Saint-Laurent (CA); Nathalie Chauret, Laval (CA); Susan E. Browne, Christiana, PA (US)

(73) Assignees: BELLUS HEALTH COUGH INC., Laval, Quebec (CA); NEOMED INSTITUTE, Montreal, Quebec (CA)

( * ) Notice: Subject to any disclaimer, the term of this patent is extended or adjusted under 35 U.S.C. 154(b) by 0 days.

(21) Appl. No.: 15/936,316

(22) Filed: Mar. 26, 2018

Related U.S. Application Data

(60) Provisional application No. 62/560,077, filed on Sep. 18, 2017.

(51) Int. Cl.
- *A61K 31/5377* (2006.01)
- *A61P 11/14* (2006.01)
- *A61K 31/437* (2006.01)
- *A61K 31/4545* (2006.01)

(52) U.S. Cl.
CPC ........ *A61K 31/5377* (2013.01); *A61K 31/437* (2013.01); *A61K 31/4545* (2013.01); *A61P 11/14* (2018.01)

(58) Field of Classification Search
CPC .............. A61K 31/5377; A61K 31/437; A61K 31/4545; A61P 11/14
See application file for complete search history.

(56) References Cited

U.S. PATENT DOCUMENTS 9,598,409 B2    3/2017   Buon et al.

OTHER PUBLICATIONS

Abdulqawi et al, Lancet, 385: 1198-205 (Year: 2015).*
Berge S.M. et al., "Pharmaceutical Salts," Journal of Pharmaceutical Science, 66:1-19, 1997.
Kamei et al., Involvement of ionotropic purinergic receptors in the histamine-induced enhancement of the cough reflex sensitivity in guinea pigs. Eur J Pharmacol 547:160-164, 2006.
Kamei et al., Involvement of P2X receptor subtypes in ATP-induced enhancement of the cough reflex sensitivity. Eur J Pharmacol 528:158-161, 2005.
Kwong et al., P2X2 receptors differentiate placodal vs. neural crest C-fiber phenotypes innervating guinea pig lungs and esophagus. AJP Lung Cell Mol Physiol., 295:L858-L865, 2008.
Mackenzie et al., Drug Discovery Today: Disease Models, 1(3):297-302, 2004.

* cited by examiner

*Primary Examiner* — Sudhakar Katakam
(74) *Attorney, Agent, or Firm* — Wilson, Sonsini, Goodrich & Rosati

(57) ABSTRACT

Provided herein are methods for the treatment of avoiding loss of taste response while treating a chronic cough patient with a selective P2X3 modulator.

19 Claims, 6 Drawing Sheets

P2X2/3 heterotrimers have major role in taste

TASTE BUDS

P2X2/3

P2X3 homotrimers have primary role in cough reflex

LARYNX, TRACHEA & BRONCHUS

ATP

| | hP2X3 (IC$_{50}$) | hP2X2/3 (IC$_{50}$) | Selectivity |
|---|---|---|---|
| Compound 1 | 11 nM | >30 μM | >2700x |
| Compound 2 | 3 nM | >30 μM | >10000x |
| Compound 9 | 127 nM | >30 μM | >236x |
| Compound 11 | 42 nM | >30 μM | >714x |
| Compound 15 | 39 nM | >30 μM | >770x |
| AF-219 | 158 nM | 241 nM | 1.5 |

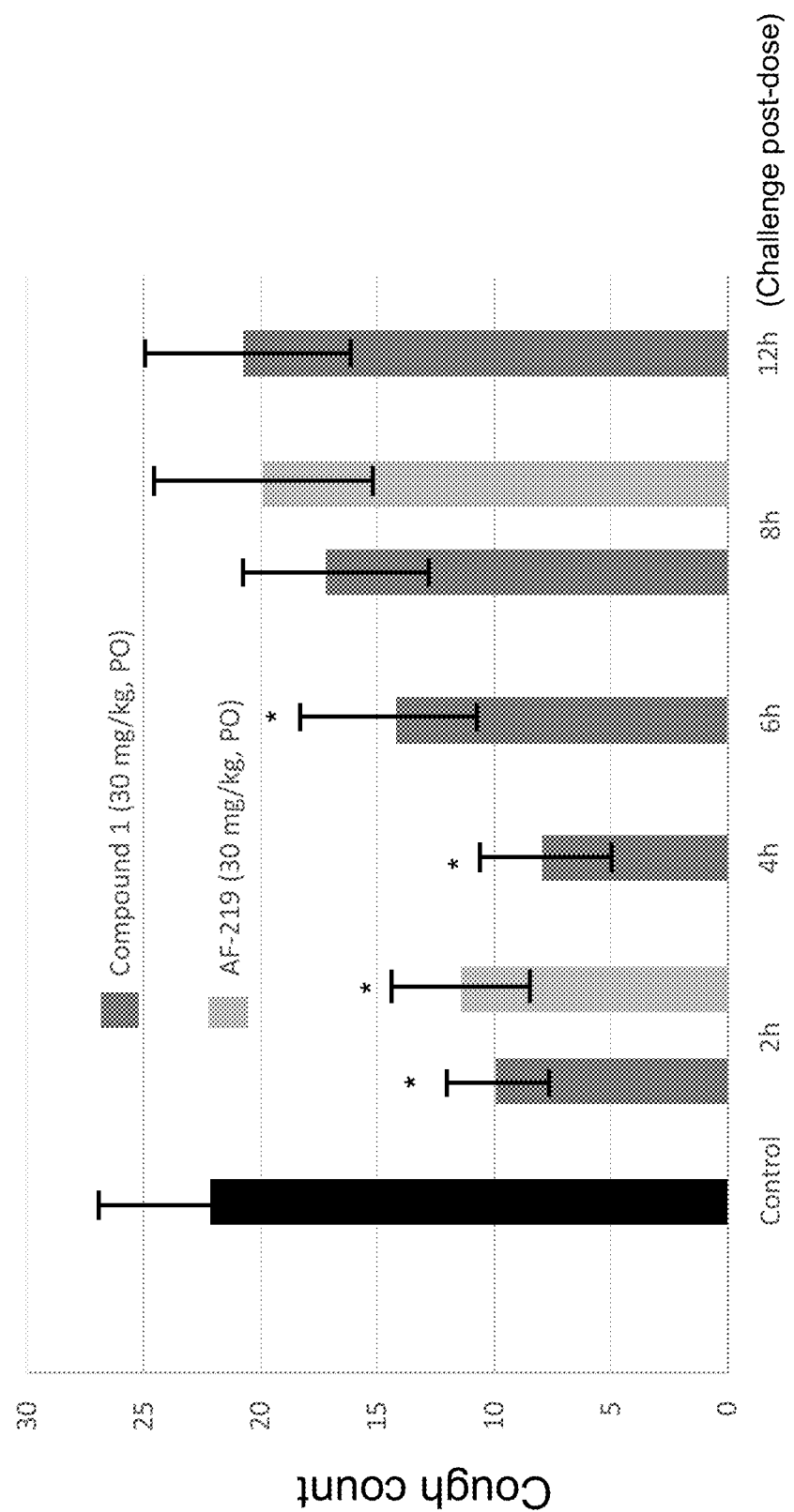

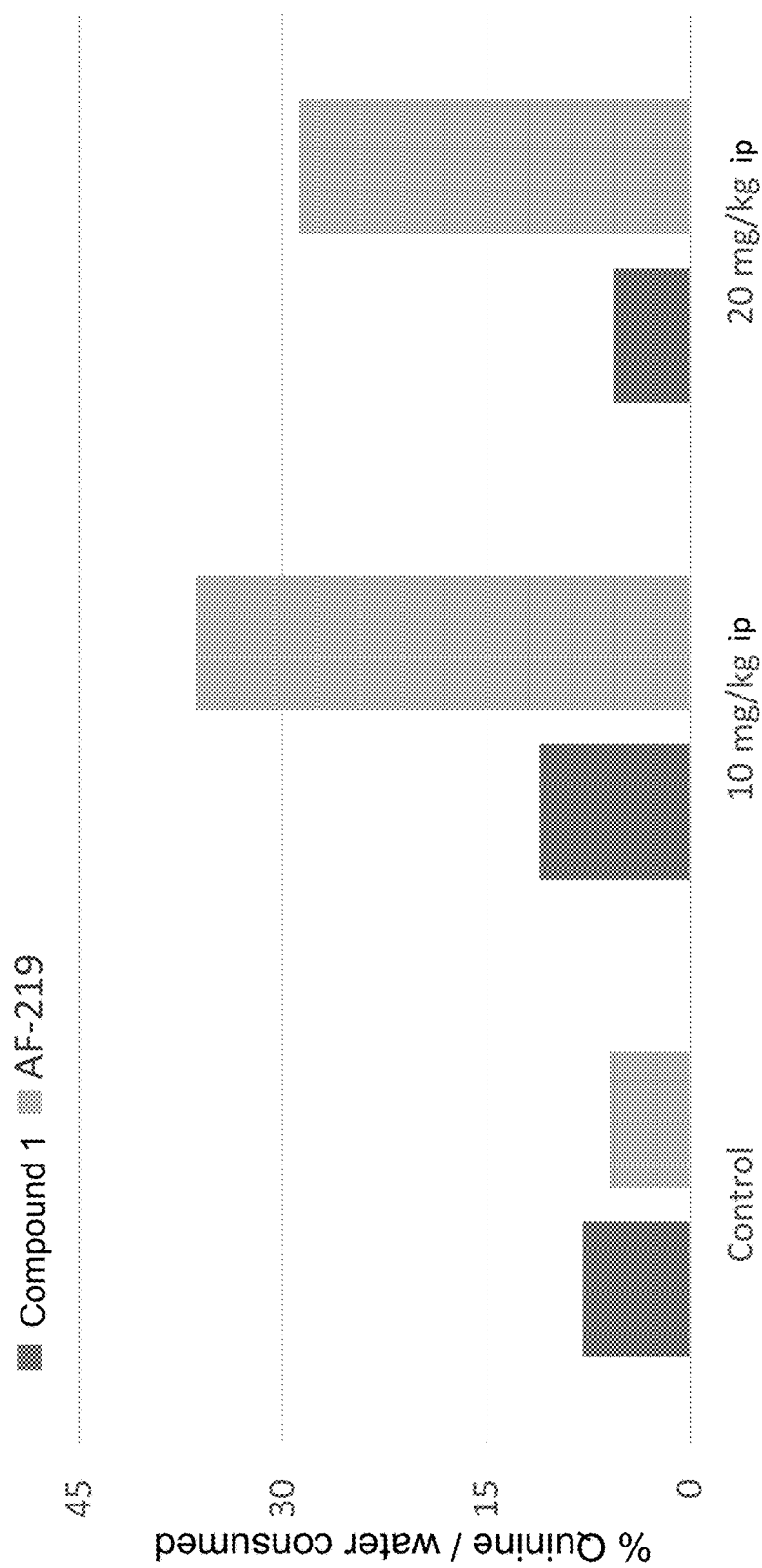

SELECTIVE P2X3 MODULATORS

CROSS-REFERENCE

This application claims benefit of U.S. Provisional Application No. 62/560,077, filed on Sep. 18, 2017, which is herein incorporated by reference in its entirety.

BACKGROUND

Chronic cough is a cough that lasts for more than eight weeks and is associated with significant adverse social, psychosocial and physical effects on quality of life. It is estimated that, in the United States alone, more than 27 million patients suffer from chronic cough. While an underlying etiology such as gastro-oesophageal reflux, asthma, or allergic rhinitis may contribute to cough in some of these patients, an underlying condition cannot be identified in 10%-40% of chronic cough patients (unexplained chronic cough). A portion of patients with an underlying condition as well as the large majority of unexplained chronic cough patients are not well controlled by current therapies.

BRIEF SUMMARY OF THE INVENTION

This disclosure provides, for example, methods of avoiding loss of taste response while treating a chronic cough patient with a selective P2X3 modulator. The disclosure also provides for the use of selective P2X3 modulators as medicaments and/or in the manufacture of medicaments for avoiding loss of taste response while treating a chronic cough patient in warm-blooded animals such as humans.

In some embodiments is a method of avoiding loss of taste response while treating a chronic cough patient, the method comprising administering to the patient a therapeutically effective amount of a selective P2X3 antagonist, wherein the selective P2X3 antagonist is at least 10-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 20-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 50-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 100-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 500-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 1000-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 2000-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 2700-fold selective for P2X3 homomeric receptor antagonism versus P2X2/3 heteromeric receptor antagonism.

In some embodiments is a method of avoiding loss of taste response while treating a chronic cough patient, the method comprising administering to the patient a therapeutically effective amount of a selective P2X3 antagonist, wherein the selective P2X3 antagonist is at least 10-fold selective, at least 20-fold selective, at least 50-fold selective, at least 100-fold selective, at least 500-fold selective, at least 1000-fold selective, at least 2000-fold selective, or at least 2700-fold selective, for P2X3 homomeric receptor antagonism versus P2X2/3 heteromeric receptor antagonism, wherein the selective P2X3 antagonist is a compound of Formula (I), or a pharmaceutically acceptable salt thereof, having the structure:

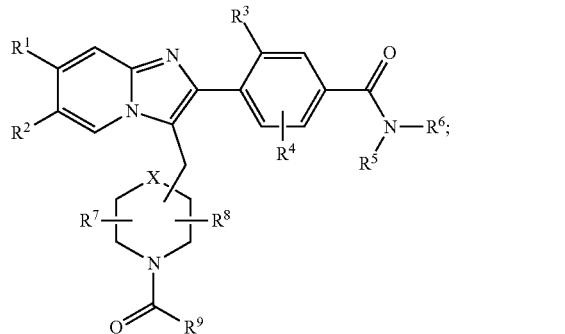

Formula (I)

wherein:

$R^1$ is selected from the group consisting of cyano, halogen, methyl, and ethyl;

$R^2$ is selected from the group consisting of hydrogen, halogen, methyl, and ethyl;

$R^3$ is selected from the group consisting of halogen, methyl, and ethyl;

$R^4$ is selected from the group consisting of hydrogen, halogen, methyl, ethyl, and methoxy;

$R^5$ and $R^6$ are independently selected from the group consisting of hydrogen, $C_1$-$C_6$-alkyl, and hydroxy-$C_1$-$C_6$-alkyl; or R[5] and R[6], together with the nitrogen to which they are both attached, form a 5- or 6-member heterocycloalkyl, wherein the heterocycloalkyl is optionally substituted with one or more substituents independently selected from the group consisting of halogen, hydroxyl, and $C_1$-$C_4$-alkyl;

R[7] and R[8] are independently selected from the group consisting of hydrogen and $C_1$-$C_4$-alkyl;

R[9] is selected from the group consisting of $C_1$-$C_6$-alkyl, $C_3$-$C_6$-cycloalkyl, $C_1$-$C_6$-alkyl-$C_3$-$C_6$-cycloalkyl, halo-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl; and X is selected from a bond, $CH_2$, and O.

In some embodiments, R[1] is methyl. In some embodiments, R[2] is hydrogen. In some embodiments, R[3] is fluoro. In some embodiments, X is O. In some embodiments, the compound of Formula (I) corresponds in structure to

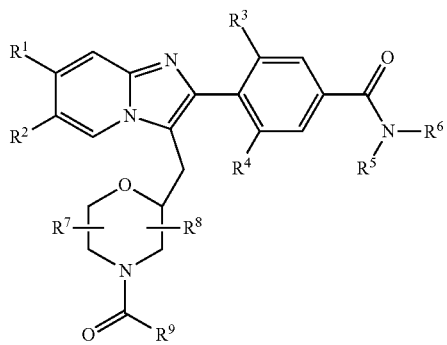

and R[4] is selected from the group consisting of halogen, methyl, and ethyl. In some embodiments, R[5] is hydrogen. In some embodiments, R[6] is $C_1$-$C_6$-alkyl. In some embodiments, R[6] is methyl. In some embodiments, R[7] is hydrogen. In some embodiments, R[8] is hydrogen. In some embodiments, R[9] is $C_1$-$C_6$-alkoxy. In some embodiments, R[9] is methoxy. In some embodiments, X is O. In some embodiments, the compound of Formula (I) corresponds in structure to

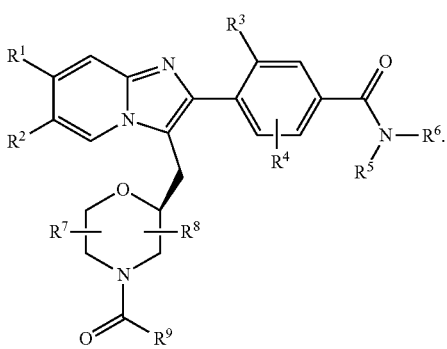

In some embodiments, the compound of Formula (I) corresponds in structure to:

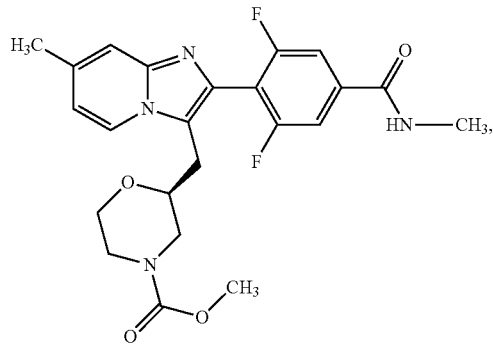
Compound 1

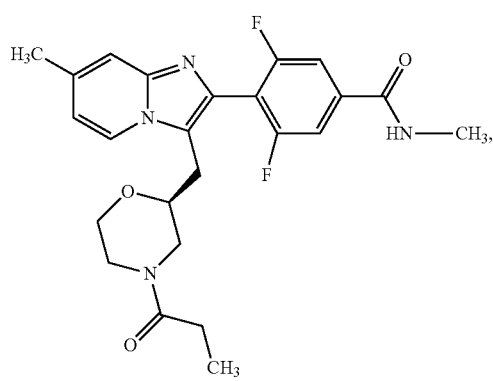
Compound 2

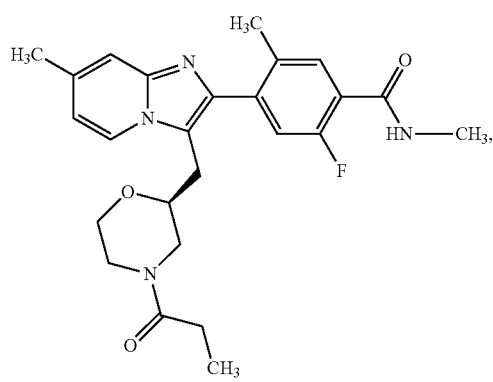
Compound 3

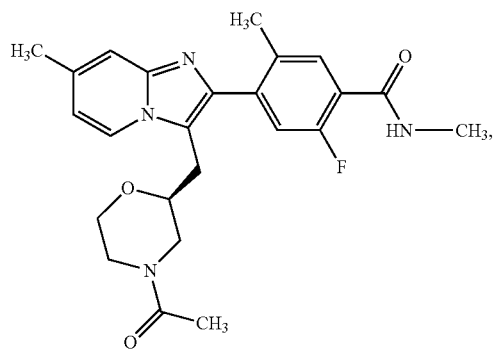
Compound 4

-continued
Compound 5
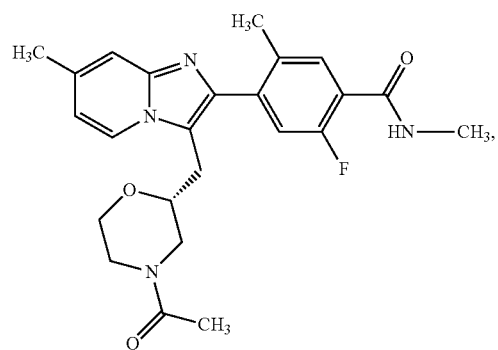
Compound 6
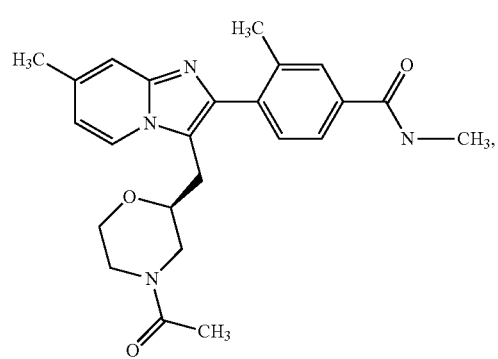
Compound 7
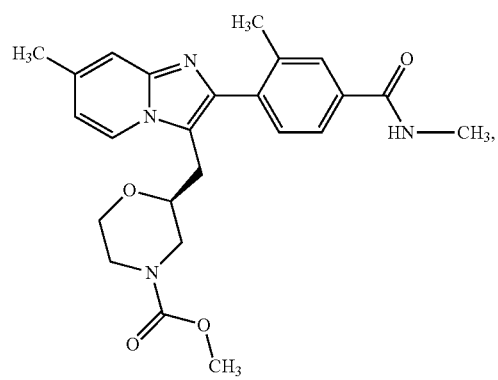
Compound 8
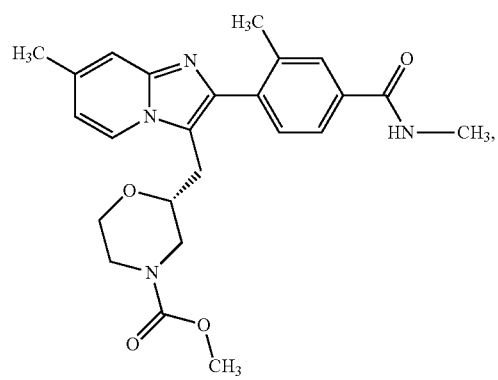
-continued
Compound 9
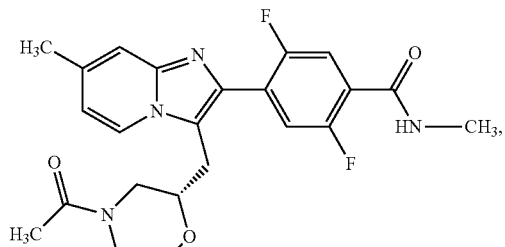
Compound 10
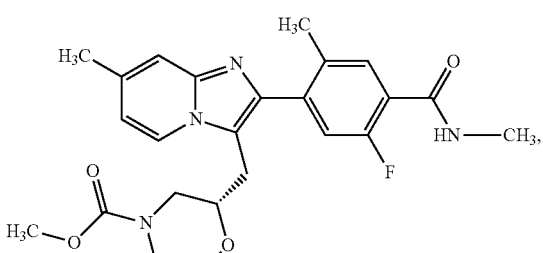
Compound 11
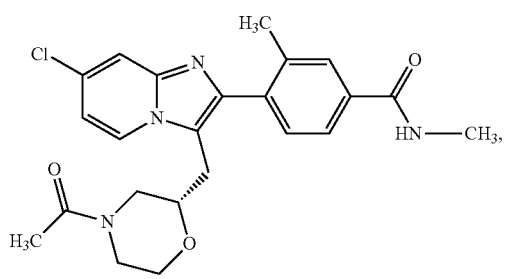
Compound 12
Compound 13
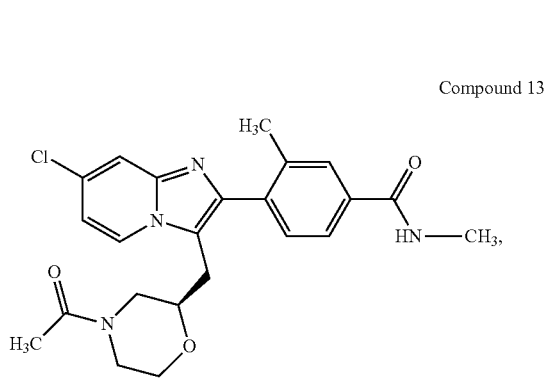

Compound 14
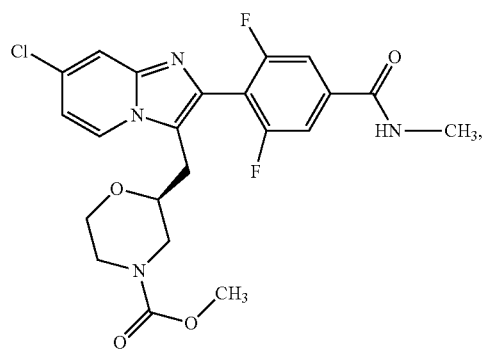
Compound 15
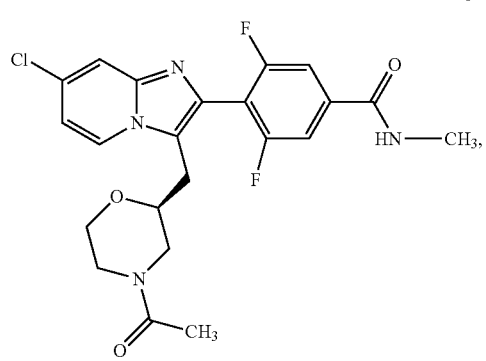
Compound 16
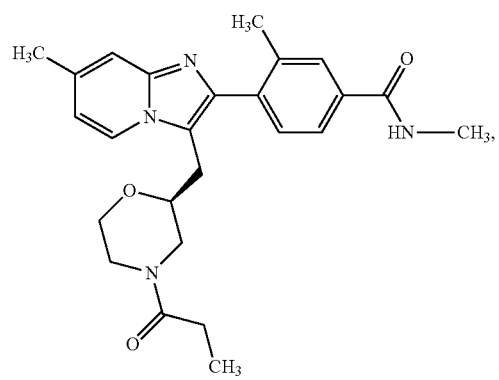
Compound 17
Compound 18
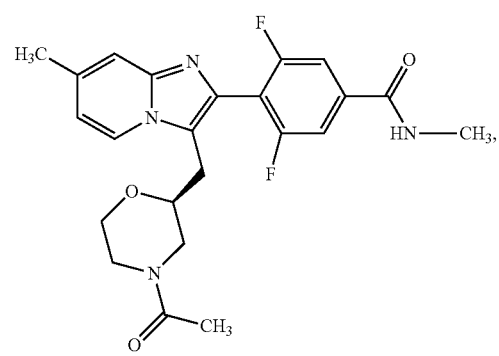
Compound 19
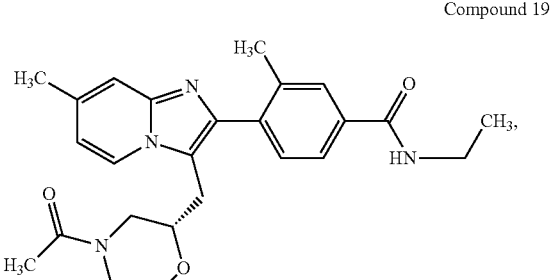
Compound 20
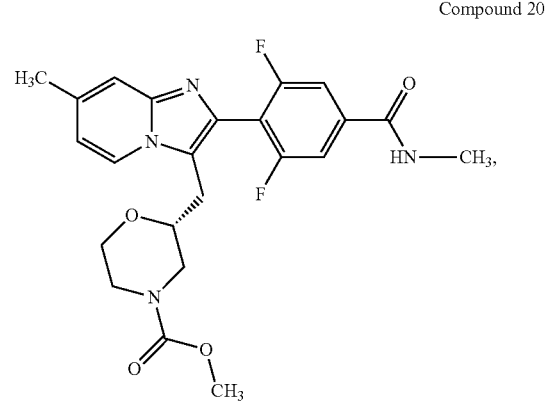
Compound 21
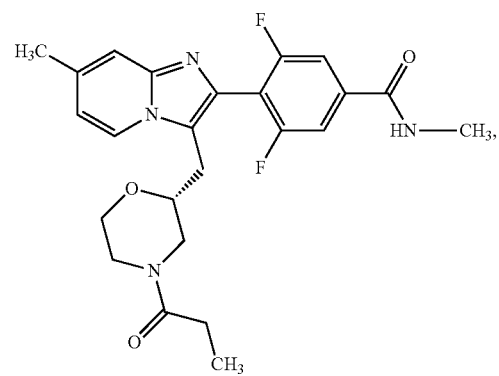

Compound 22
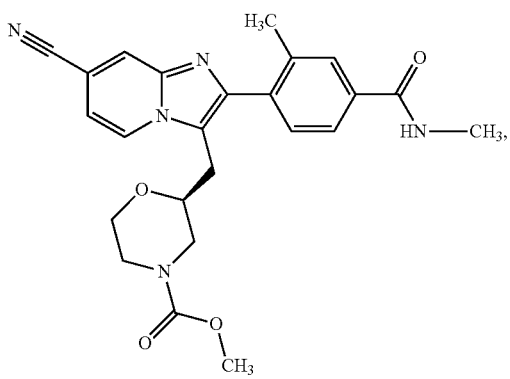
Compound 23
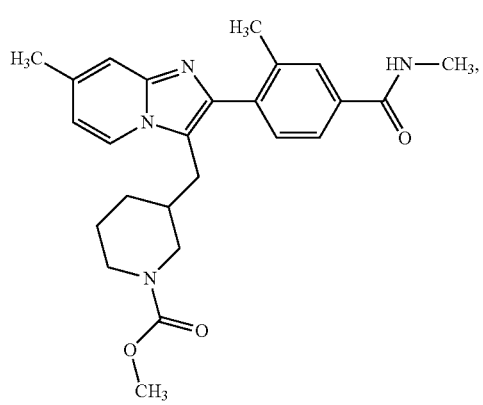
Compound 24
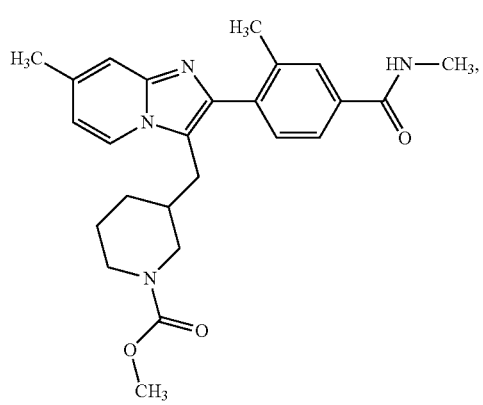
Compound 25
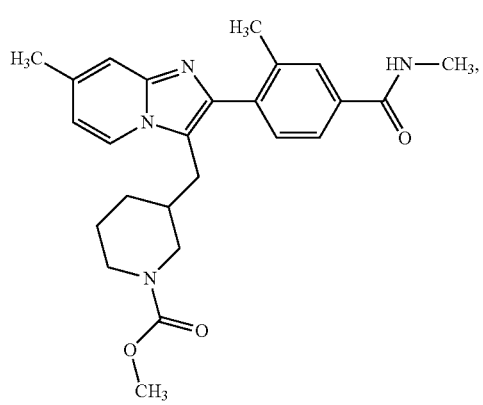
Compound 26
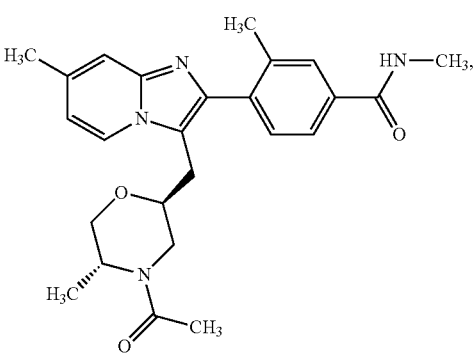
Compound 27
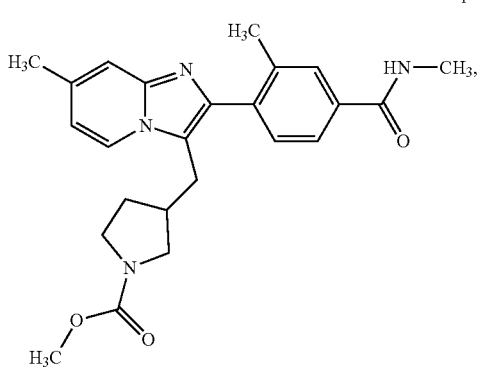
Compound 28
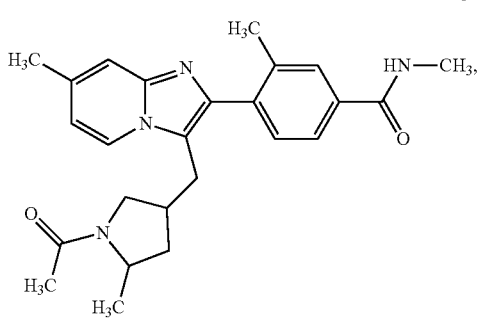
Compound 29
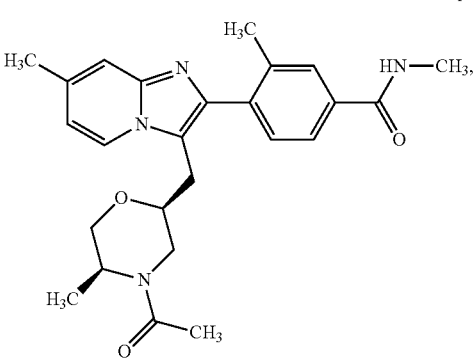

Compound 30
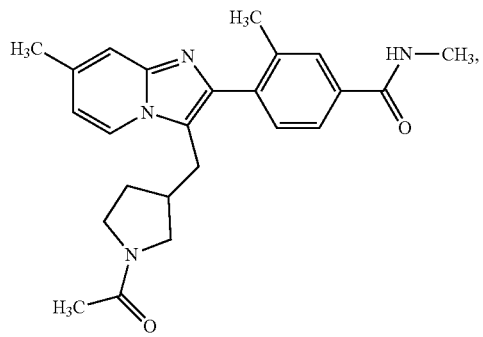

Compound 31
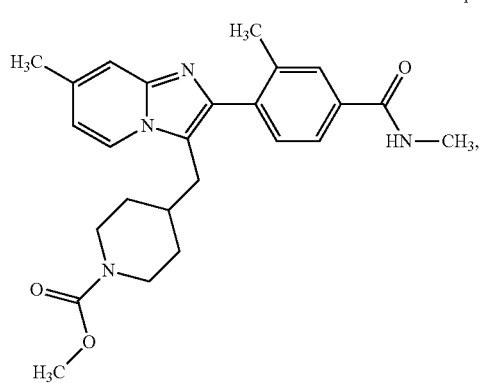

Compound 32
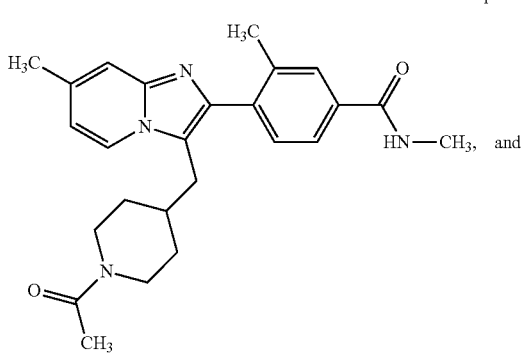, and

Compound 33
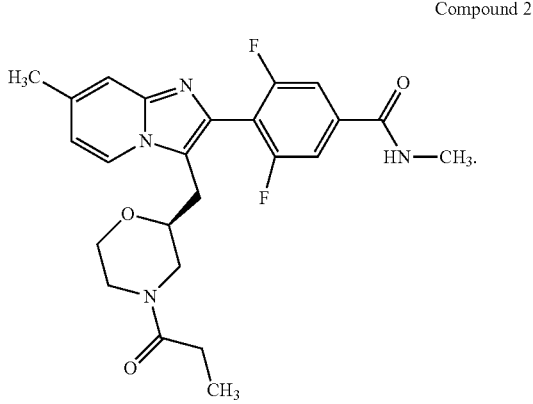 [SMILES: CCC(=O)N1CCO[C@@H](Cc2c(-c3c(F)cc(C(=O)NC)cc3F)nc3cc(C)ccn23)C1]

In some embodiments, the compound of Formula (I) corresponds in structure to

Compound 1
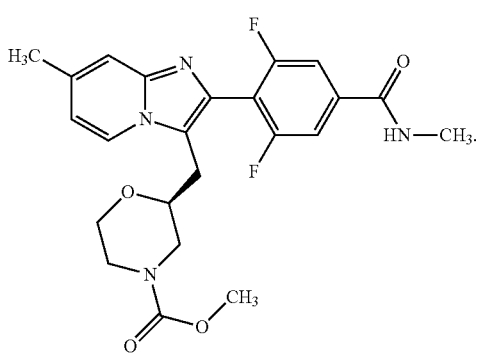

In some embodiments, the compound of Formula (I) corresponds in structure to

Compound 20
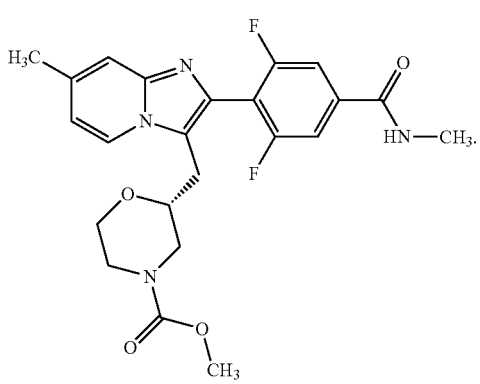

In some embodiments, the compound of Formula (I) corresponds in structure to

Compound 2

In some embodiments, the compound of Formula (I) corresponds in structure to

Compound 21

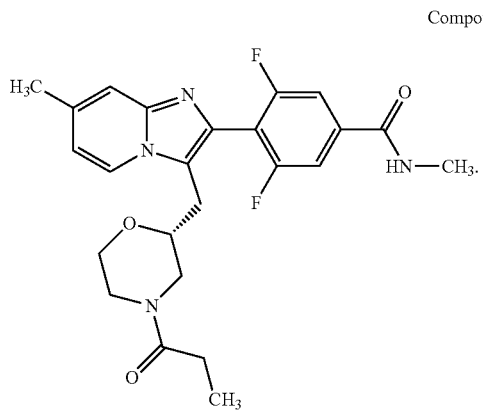

In some embodiments, the compound of Formula (I) corresponds in structure to

Compound 34

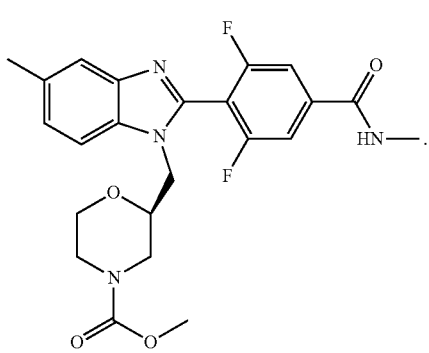

In some embodiments, the compound of Formula (I) corresponds in structure to

Compound 35

In some embodiments, the compound of Formula (I) corresponds in structure to

Compound 36

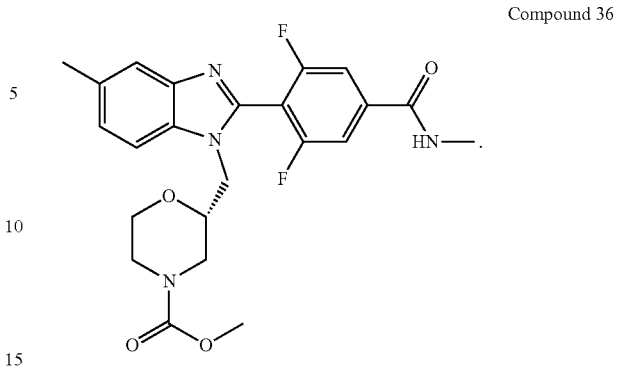

BRIEF DESCRIPTION OF THE DRAWINGS

FIG. 3 shows the potency and selectivity of Compound 1 and Gefapixant (also know as AF-219) for human P2X3 and P2X2/3 receptors.

FIG. 5 shows the duration of the anti-tussive effect of Compound 1 and AF-219 in a time course study of a guinea pig cough model.

FIG. 6 shows the effect on taste function of Compound 1 and AF-219 in a two bottle rat taste study.

DETAILED DESCRIPTION OF THE INVENTION

P2X2 receptors and P2X3 receptors are homotrimers containing 3 subunits of P2X2 and P2X3, respectively. P2X2/3 receptors are heterotrimers, containing a mix of P2X3 and P2X2 subunits. Compounds can have differential effects, in terms of potency and/or maximal inhibition, with respect to their ability to inhibit P2X3 homomers vs. P2X2/3 heteromers. Thus, the effect of a compound on a cell will depend on the mixture of receptors that cell expresses (P2X3 homomers, P2X2 homomers, or P2X2/3 heteromers) and the drug's selectivity for the various P2X subtypes.

Figure 1:
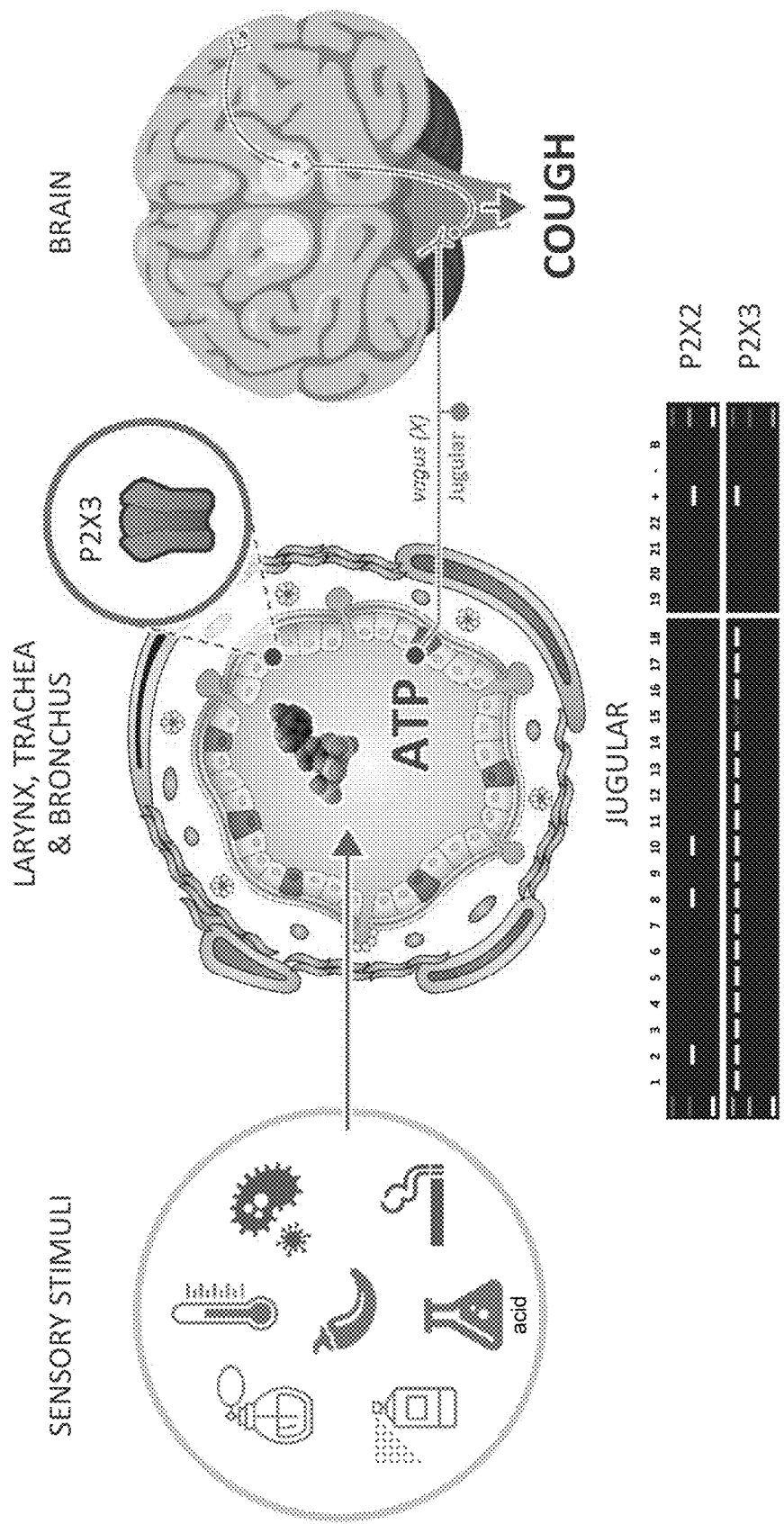
FIG. 1 depicts the role of P2X3 receptors in chronic cough.
Figure 2:
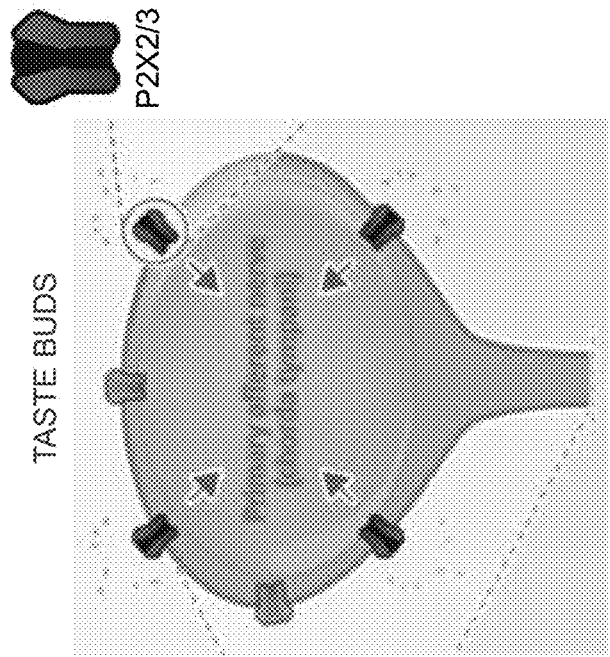
FIG. 2 depicts the roles of P2X3 and P2X2/3 receptors in chronic cough and taste function.
Figure 2:
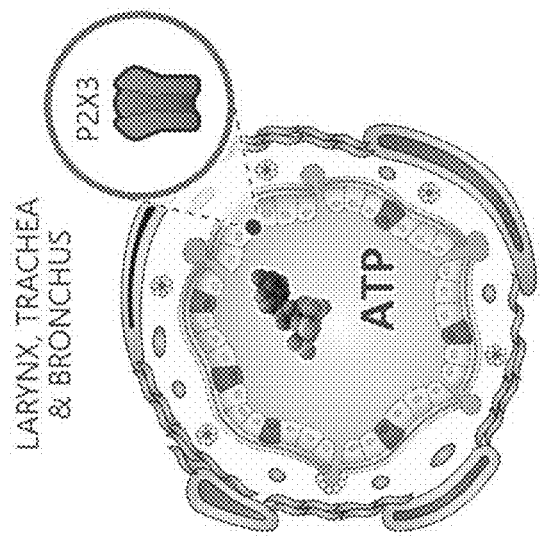

In chronic cough, the majority of stimuli triggering cough are affecting the upper airways (e.g. strong odor/smoke, cold air, post-nasal drips, aspiration of gastroesophageal reflux, speaking). Furthermore, the greatest concentration of cough receptors is in the larynx, carina and bifurcation of the medium to large-sized bronchi. These observations indicate that the upper airways play a major role in cough. Therefore, given that upper airways are innervated by jugular C-fibres that express primarily P2X3 channels, it suggests that P2X3 homotrimeric receptors are responsible for the increase in cough reflex sensitivity (FIG. 1; P2X2 vs. P2X3 expression adapted from Kwong et al 2008 AJP Lung cell Mol Physiol 295 L858-65). Whereas P2X3 receptors have a primary role in the cough reflex, P2X2/3 receptors have a major role in taste function (FIG. 2). Immunohistochemical staining of the nerve fibres innervating the taste buds of rats showed the presence of both P2X2 and P2X3 subunits and studies of double knock-out mice suggest that P2X2/3 heteromeric receptors are an important component of taste signal transduction. As such, this disclosure is directed, at least in part, to a method of avoiding loss of taste response while treating a chronic cough patient, the method comprising administering to the patient a therapeutically effective amount of a P2X3 antagonist which is selective versus P2X2/3.

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_{1-5}$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)$R^a$, —N($R^a$)$_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)R$^f$, —N($R^a$)S(O)$_t$R$^f$ (where t is 1 or 2), —S(O)$_t$O$R^a$ (where t is 1 or 2), —S(O)$_t$R$^f$ (where t is 1 or 2) and —S(O)$_t$N($R^a$)$_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—R$^f$, —N($R^a$)$_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)R$^f$, —N($R^a$)S(O)$_t$R$^f$ (where t is 1 or 2), —S(O)$_t$O$R^a$ (where t is 1 or 2), —S(O)$_t$R$^f$ (where t is 1 or 2) and —S(O)$_t$N($R^a$)$_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)$R^a$, —N($R^a$)$_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)R$^f$, —N($R^a$)S(O)$_t$R$^f$ (where t is 1 or 2), —S(O)$_t$O$R^a$ (where t is 1 or 2), —S(O)$_t$R$^f$ (where t is 1 or 2) and —S(O)$_t$N($R^a$)$_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each R$^f$ is independently alkyl, fluoroalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)$ $R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)$ $R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O) $R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, he compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

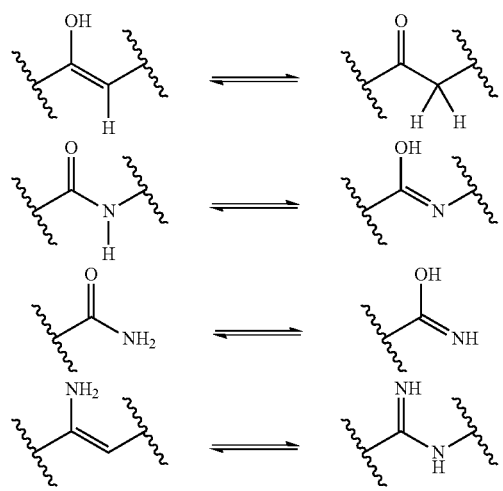

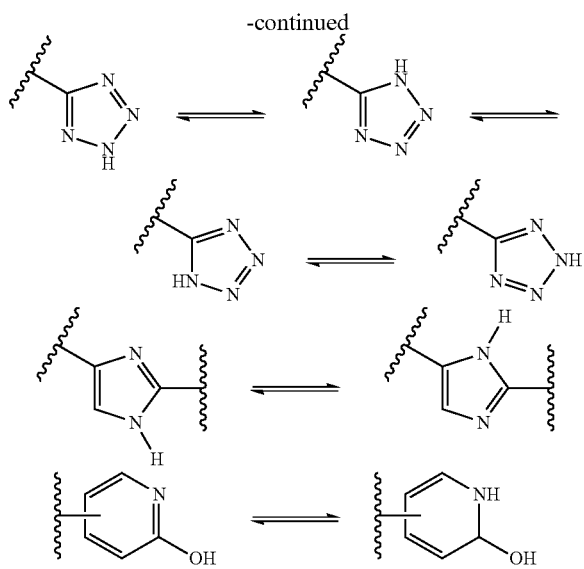

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

As used herein, "loss of taste response while treating a chronic cough patient" refers to any loss of a patient's taste response while being treating for chronic cough. In some embodiments, the patient's loss of taste response is a 10% loss. In some embodiments, the patient's loss of taste response is a 20% loss. In some embodiments, the patient's loss of taste response is a 30% loss. In some embodiments, the patient's loss of taste response is a 40% loss. In some embodiments, the patient's loss of taste response is a 50% loss. In some embodiments, the patient's loss of taste response is a 60% loss. In some embodiments, the patient's loss of taste response is a 70% loss. In some embodiments, the patient's loss of taste response is a 80% loss. In some embodiments, the patient's loss of taste response is a 90% loss. In some embodiments, the patient's loss of taste response is a 100% loss. In some embodiments, the patient's loss of taste response refers to an alteration of patient's taste response.

Methods

In some embodiments disclosed herein are methods of avoiding loss of taste response while treating a chronic cough patient. In some embodiments, is a method of avoiding loss of taste response while treating a chronic cough patient, the method comprising administering to the patient a therapeutically effective amount of a selective P2X3 antagonist, wherein the selective P2X3 antagonist is selective for P2X3 homomeric receptor antagonism versus P2X2/3 heteromeric receptor antagonism. In some embodiments, is a method of avoiding loss of taste response while treating a chronic cough patient, the method comprising administering to the patient a therapeutically effective amount of a selective P2X3 antagonist, wherein the selective P2X3 antagonist is at least 10-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 20-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 20-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 30-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 40-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 50-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 60-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 70-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 80-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 90-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 100-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 150-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 200-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 250-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 300-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 350-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 400-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 450-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 500-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 600-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 700-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 800-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 900-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 1000-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 1200-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 1400-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 1600-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 1800-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 2000-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 2200-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 2500-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 2700-fold selective for P2X3 homomeric receptor antagonism versus P2X2/3 heteromeric receptor antagonism. In some embodiments is a method of avoiding loss of taste response while treating a chronic cough patient, the method comprising administering to the patient a therapeutically effective amount of a selective P2X3 antagonist, wherein the selective P2X3 antagonist is at least 3000-fold selective for P2X3 homomeric receptor antagonism versus P2X2/3 heteromeric receptor antagonism.

In some embodiments is a method of avoiding loss of taste response while treating a chronic cough patient, the method comprising administering to the patient a therapeutically effective amount of a selective P2X3 antagonist, wherein the selective P2X3 antagonist is a compound of Formula (I), or a pharmaceutically acceptable salt thereof, having the structure:

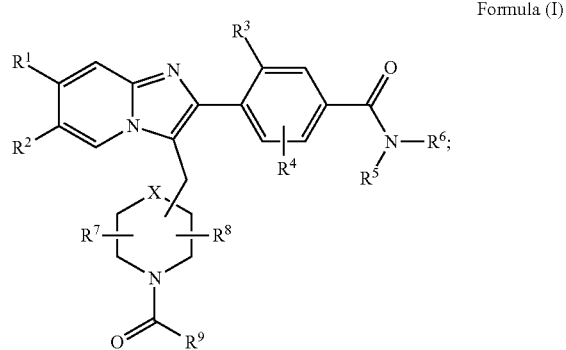

Formula (I)

wherein:
$R^1$ is selected from the group consisting of cyano, halogen, methyl, and ethyl;
$R^2$ is selected from the group consisting of hydrogen, halogen, methyl, and ethyl;
$R^3$ is selected from the group consisting of halogen, methyl, and ethyl;
$R^4$ is selected from the group consisting of hydrogen, halogen, methyl, ethyl, and methoxy;
$R^5$ and $R^6$ are independently selected from the group consisting of hydrogen, $C_1$-$C_6$-alkyl, and hydroxy-$C_1$-$C_6$-alkyl; or
$R^5$ and $R^6$, together with the nitrogen to which they are both attached, form a 5- or 6-member heterocycloalkyl, wherein the heterocycloalkyl is optionally substituted with one or more substituents independently selected from the group consisting of halogen, hydroxyl, and $C_1$-$C_4$-alkyl;

R⁷ and R⁸ are independently selected from the group consisting of hydrogen and $C_1$-$C_4$-alkyl;

R⁹ is selected from the group consisting of $C_1$-$C_6$-alkyl, $C_3$-$C_6$-cycloalkyl, $C_1$-$C_6$-alkyl-$C_3$-$C_6$-cycloalkyl, halo-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl; and X is selected from a bond, $CH_2$, and O.

In some embodiments of the methods described herein, the selective P2X3 antagonist is a compound of Formula (I), or a pharmaceutically acceptable salt thereof, wherein X is a bond. In some embodiments of the methods described herein, the selective P2X3 antagonist is a compound of Formula (I), or a pharmaceutically acceptable salt thereof, wherein X is $CH_2$. In some embodiments of the methods described herein, the selective P2X3 antagonist is a compound of Formula (I), or a pharmaceutically acceptable salt thereof, wherein X is O.

In some embodiments of the methods described herein, the selective P2X3 antagonist is a compound of Formula (I), or a pharmaceutically acceptable salt thereof, wherein $R^1$ is cyano. In some embodiments of the methods described herein, the selective P2X3 antagonist is a compound of Formula (I), or a pharmaceutically acceptable salt thereof, wherein $R^1$ is halogen. In some embodiments of the methods described herein, the selective P2X3 antagonist is a compound of Formula (I), or a pharmaceutically acceptable salt thereof, wherein $R^1$ is methyl. In some embodiments of the methods described herein, the selective P2X3 antagonist is a compound of Formula (I), or a pharmaceutically acceptable salt thereof, wherein $R^1$ is ethyl.

In some embodiments of the methods described herein, the selective P2X3 antagonist is a compound of Formula (I), or a pharmaceutically acceptable salt thereof, wherein $R^2$ is hydrogen. In some embodiments of the methods described herein, the selective P2X3 antagonist is a compound of Formula (I), or a pharmaceutically acceptable salt thereof, wherein $R^2$ is halogen. In some embodiments of the methods described herein, the selective P2X3 antagonist is a compound of Formula (I), or a pharmaceutically acceptable salt thereof, wherein $R^2$ is methyl. In some embodiments of the methods described herein, the selective P2X3 antagonist is a compound of Formula (I), or a pharmaceutically acceptable salt thereof, wherein $R^2$ is ethyl.

In some embodiments of the methods described herein, the selective P2X3 antagonist is a compound of Formula (I), or a pharmaceutically acceptable salt thereof, wherein $R^3$ is halogen. In some embodiments of the methods described herein, the selective P2X3 antagonist is a compound of Formula (I), or a pharmaceutically acceptable salt thereof, wherein $R^3$ is fluoro. In some embodiments of the methods described herein, the selective P2X3 antagonist is a compound of Formula (I), or a pharmaceutically acceptable salt thereof, wherein $R^3$ is methyl. In some embodiments of the methods described herein, the selective P2X3 antagonist is a compound of Formula (I), or a pharmaceutically acceptable salt thereof, wherein $R^3$ is ethyl.

In some embodiments of the methods described herein, the selective P2X3 antagonist is a compound of Formula (I), or a pharmaceutically acceptable salt thereof, wherein $R^4$ is hydrogen. In some embodiments of the methods described herein, the selective P2X3 antagonist is a compound of Formula (I), or a pharmaceutically acceptable salt thereof, wherein $R^4$ is halogen. In some embodiments of the methods described herein, the selective P2X3 antagonist is a compound of Formula (I), or a pharmaceutically acceptable salt thereof, wherein $R^4$ is fluoro. In some embodiments of the methods described herein, the selective P2X3 antagonist is a compound of Formula (I), or a pharmaceutically acceptable salt thereof, wherein $R^4$ is methyl. In some embodiments of the methods described herein, the selective P2X3 antagonist is a compound of Formula (I), or a pharmaceutically acceptable salt thereof, wherein $R^4$ is ethyl. In some embodiments of the methods described herein, the selective P2X3 antagonist is a compound of Formula (I), or a pharmaceutically acceptable salt thereof, wherein $R^4$ is methoxy.

In some embodiments of the methods described herein, the selective P2X3 antagonist is a compound of Formula (I), or a pharmaceutically acceptable salt thereof, wherein $R^5$ and $R^6$ are independently selected from the group consisting of hydrogen and $C_1$-$C_6$-alkyl. In some embodiments of the methods described herein, the selective P2X3 antagonist is a compound of Formula (I), or a pharmaceutically acceptable salt thereof, wherein $R^5$ and $R^6$ are each hydrogen. In some embodiments of the methods described herein, the selective P2X3 antagonist is a compound of Formula (I), or a pharmaceutically acceptable salt thereof, wherein $R^5$ and $R^6$ are each $C_1$-$C_6$-alkyl. In some embodiments of the methods described herein, the selective P2X3 antagonist is a compound of Formula (I), or a pharmaceutically acceptable salt thereof, wherein $R^5$ is hydrogen and $R^6$ is $C_1$-$C_6$-alkyl. In some embodiments of the methods described herein, the selective P2X3 antagonist is a compound of Formula (I), or a pharmaceutically acceptable salt thereof, wherein $R^5$ is hydrogen and $R^6$ is methyl.

In some embodiments of the methods described herein, the selective P2X3 antagonist is a compound of Formula (I), or a pharmaceutically acceptable salt thereof, wherein $R^7$ and $R^8$ are independently selected from the group consisting of hydrogen and methyl. In some embodiments of the methods described herein, the selective P2X3 antagonist is a compound of Formula (I), or a pharmaceutically acceptable salt thereof, wherein $R^7$ and $R^8$ are each hydrogen. In some embodiments of the methods described herein, the selective P2X3 antagonist is a compound of Formula (I), or a pharmaceutically acceptable salt thereof, wherein $R^7$ is hydrogen and $R^8$ is methyl.

In some embodiments of the methods described herein, the selective P2X3 antagonist is a compound of Formula (I), or a pharmaceutically acceptable salt thereof, wherein $R^9$ is selected from the group consisting of $C_1$-$C_6$-alkyl and $C_1$-$C_6$-alkoxy. In some embodiments of the methods described herein, the selective P2X3 antagonist is a compound of Formula (I), or a pharmaceutically acceptable salt thereof, wherein $R^9$ is $C_1$-$C_6$-alkyl. In some embodiments of the methods described herein, the selective P2X3 antagonist is a compound of Formula (I), or a pharmaceutically acceptable salt thereof, wherein $R^9$ is methyl. In some embodiments of the methods described herein, the selective P2X3 antagonist is a compound of Formula (I), or a pharmaceutically acceptable salt thereof, wherein $R^9$ is ethyl. In some embodiments of the methods described herein, the selective P2X3 antagonist is a compound of Formula (I), or a pharmaceutically acceptable salt thereof, wherein $R^9$ is $C_1$-$C_6$-alkoxy. In some embodiments of the methods described herein, the selective P2X3 antagonist is a compound of Formula (I), or a pharmaceutically acceptable salt thereof, wherein $R^9$ is methoxy.

In some embodiments of the methods described herein, the selective P2X3 antagonist is a compound of Formula (I), or a pharmaceutically acceptable salt thereof, wherein the compound of Formula (I) corresponds in structure to

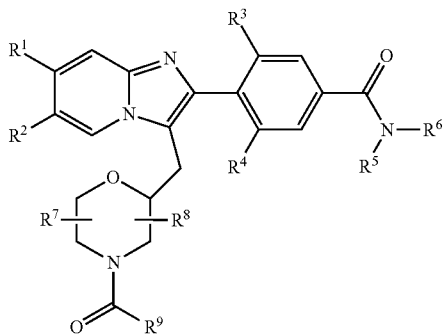

and $R^4$ is selected from the group consisting of halogen, methyl, and ethyl. In some embodiments of the methods described herein, the selective P2X3 antagonist is a compound of Formula (I), or a pharmaceutically acceptable salt thereof, wherein the compound of Formula (I) corresponds in structure to

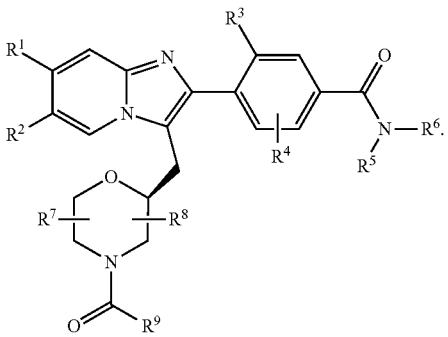

In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is halogen, $R^4$ is halogen, $R^5$ is hydrogen, $R^6$ is $C_1$-$C_6$-alkyl, $R^7$ is hydrogen, $R^8$ is hydrogen, and $R^9$ is $C_1$-$C_6$-alkyl. In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is fluoro, $R^4$ is fluoro, $R^5$ is hydrogen, $R^6$ is methyl, $R^7$ is hydrogen, $R^8$ is hydrogen, and $R^9$ is methyl.

In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is halogen, $R^4$ is halogen, $R^5$ is hydrogen, $R^6$ is $C_1$-$C_6$-alkyl, $R^7$ is hydrogen, $R^8$ is hydrogen, and $R^9$ is $C_1$-$C_6$-alkoxy. In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is fluoro, $R^4$ is fluoro, $R^5$ is hydrogen, $R^6$ is methyl, $R^7$ is hydrogen, $R^8$ is hydrogen, and $R^9$ is methoxy.

In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is methyl, $R^4$ is hydrogen, $R^5$ is hydrogen, $R^6$ is $C_1$-$C_6$-alkyl, $R^7$ is hydrogen, $R^8$ is hydrogen, and $R^9$ is $C_1$-$C_6$-alkyl. In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is methyl, $R^4$ is hydrogen, $R^5$ is hydrogen, $R^6$ is methyl, $R^7$ is hydrogen, $R^8$ is hydrogen, and $R^9$ is methyl.

In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is methyl, $R^4$ is hydrogen, $R^5$ is hydrogen, $R^6$ is $C_1$-$C_6$-alkyl, $R^7$ is hydrogen, $R^8$ is hydrogen, and $R^9$ is $C_1$-$C_6$-alkoxy. In some embodiments of the methods described herein, the selective P2X3 antagonist is a compound of Formula (I), or a pharmaceutically acceptable salt thereof, wherein X is O, $R^1$ is methyl, $R^2$ is hydrogen, $R^3$ is methyl, $R^4$ is hydrogen, $R^5$ is hydrogen, $R^6$ is methyl, $R^7$ is hydrogen, $R^8$ is hydrogen, and $R^9$ is methoxy.

In some embodiments of the methods described herein, the selective P2X3 antagonist is a compound of Formula (I), or a pharmaceutically acceptable salt thereof, wherein the compound of Formula (I) corresponds in structure to:

Compound 1

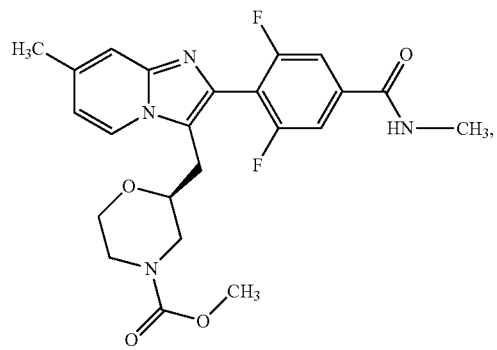

Compound 2

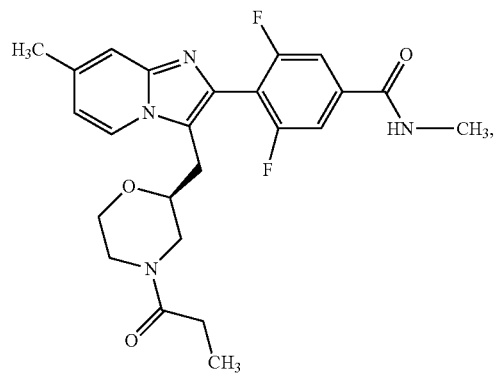

Compound 3

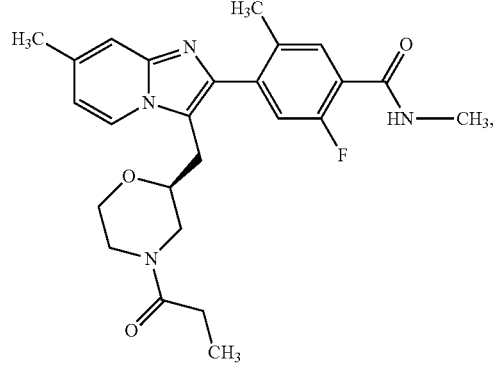

-continued
Compound 4
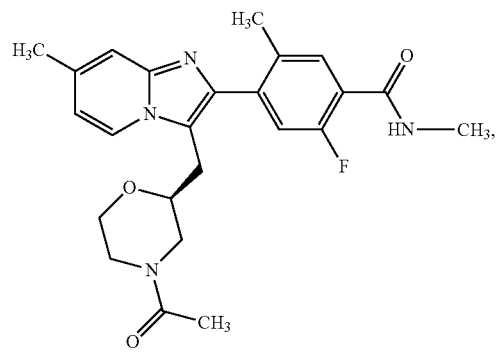
Compound 5
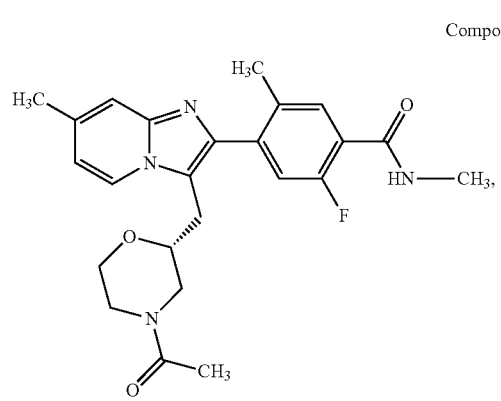
Compound 6
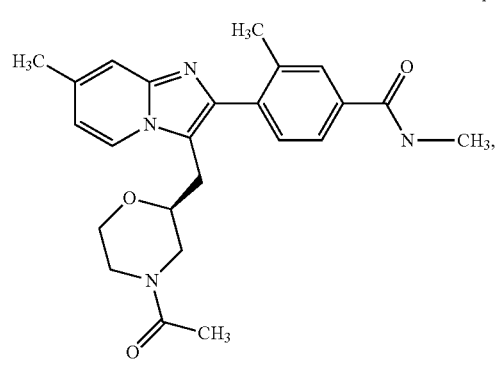
Compound 7
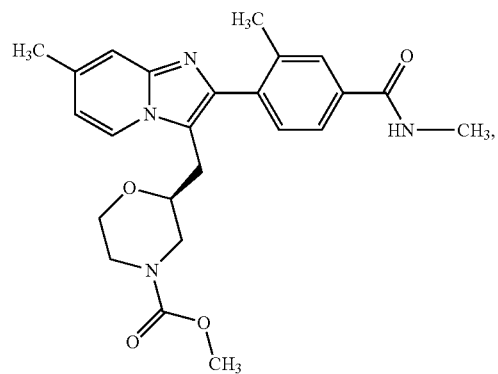
-continued
Compound 8
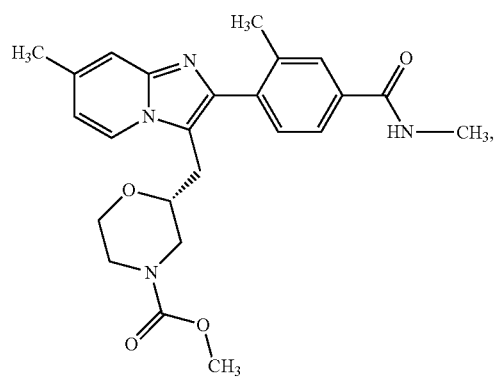
Compound 9
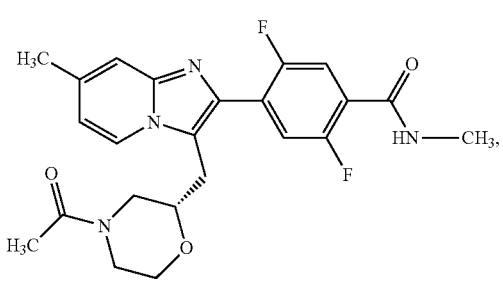
Compound 10
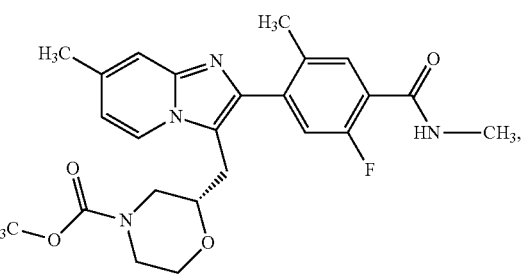
Compound 11
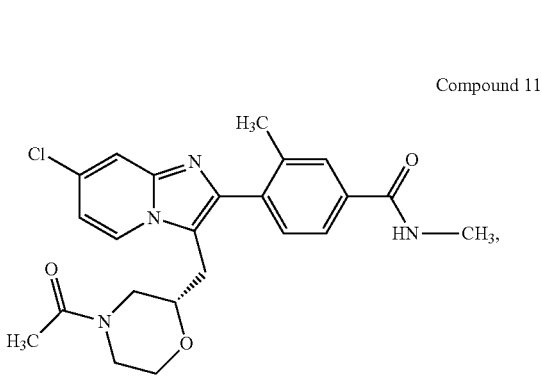

Compound 12
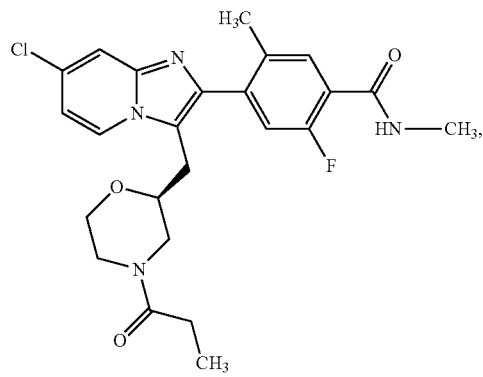
Compound 13
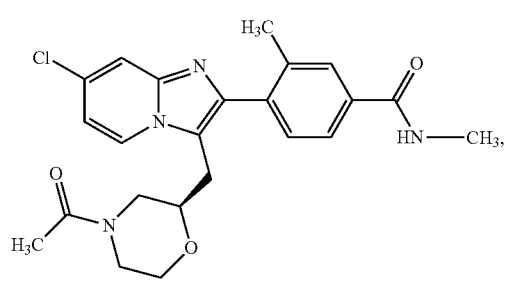
Compound 14
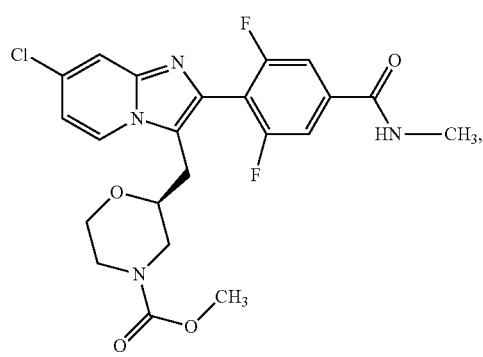
Compound 15
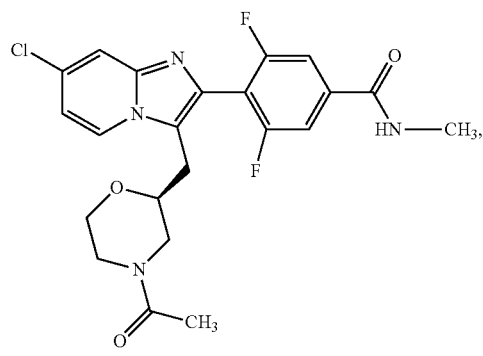
Compound 16
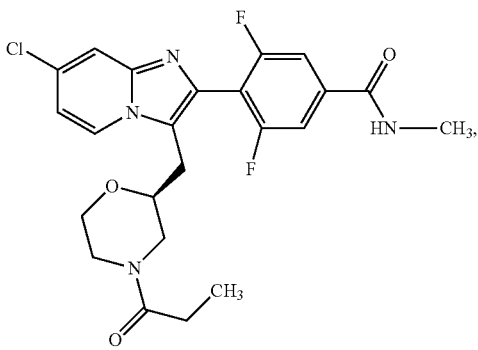
Compound 17
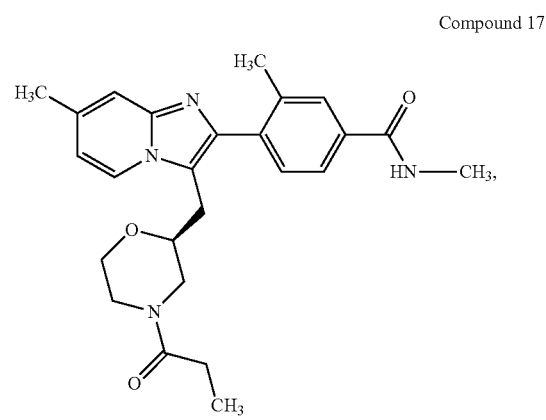
Compound 18
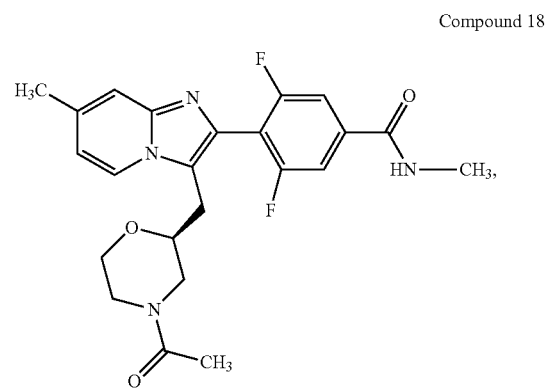
Compound 19
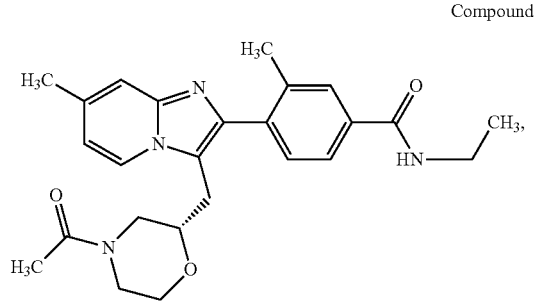

Compound 20
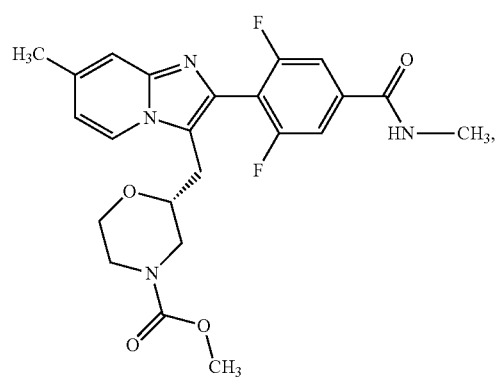
Compound 21
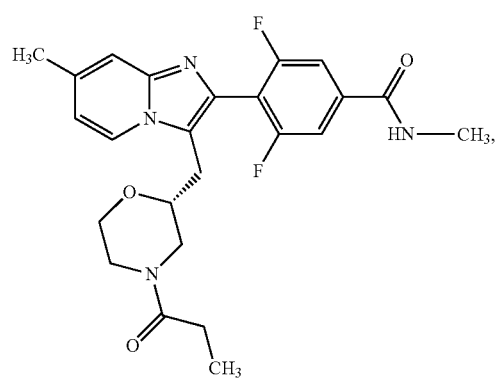
Compound 22
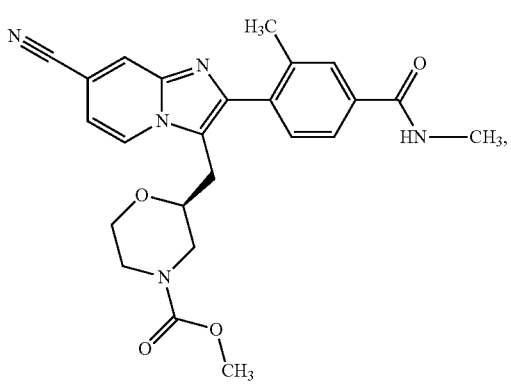
Compound 23
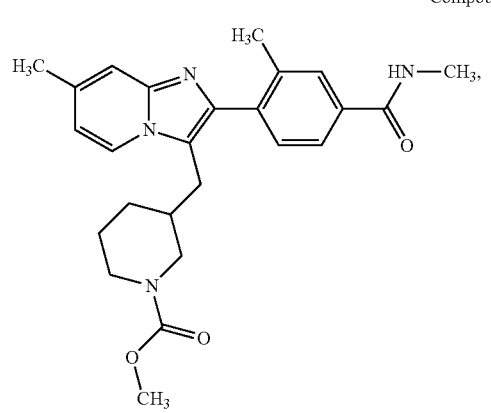
Compound 24
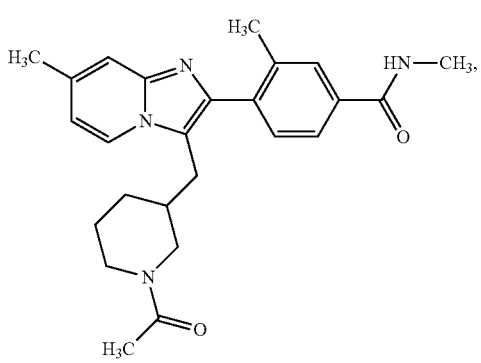
Compound 25
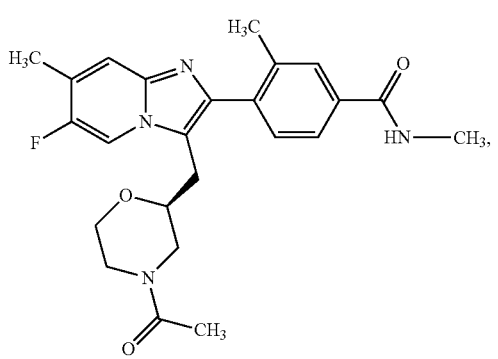
Compound 26
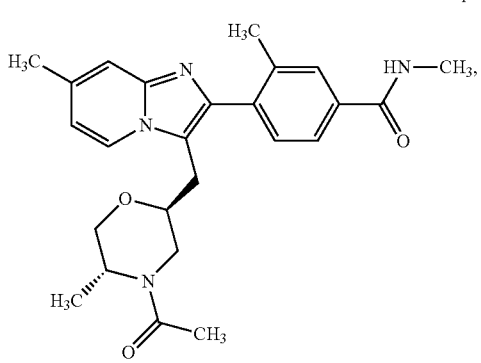
Compound 27
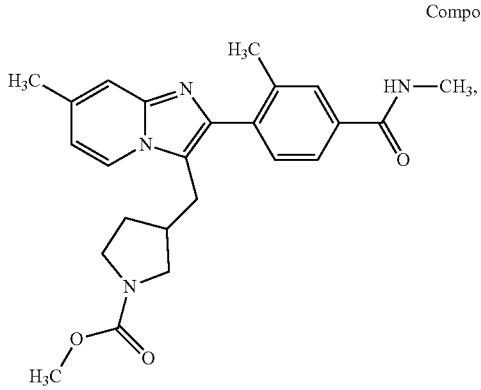

Compound 28

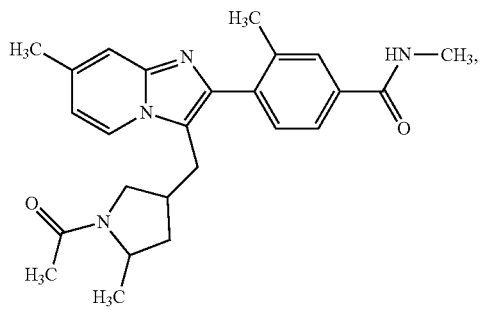

Compound 29

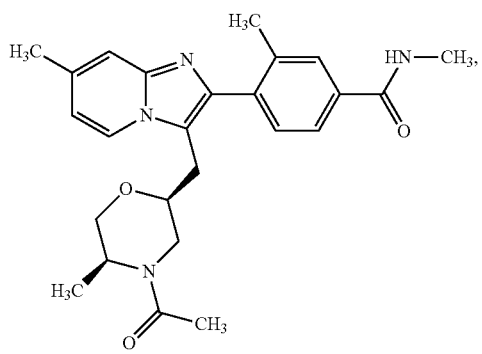

Compound 30

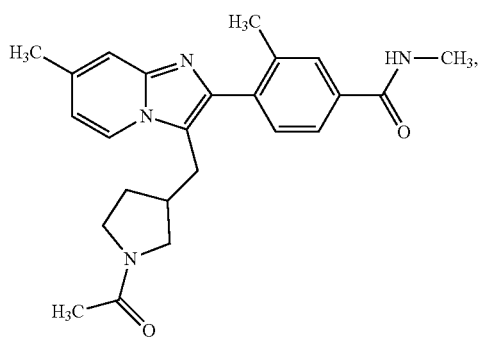

Compound 31

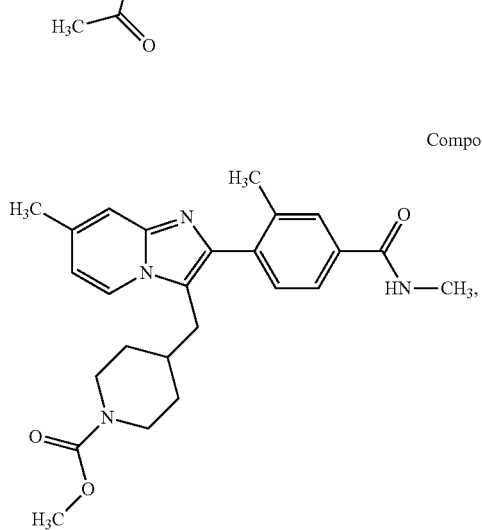

Compound 32

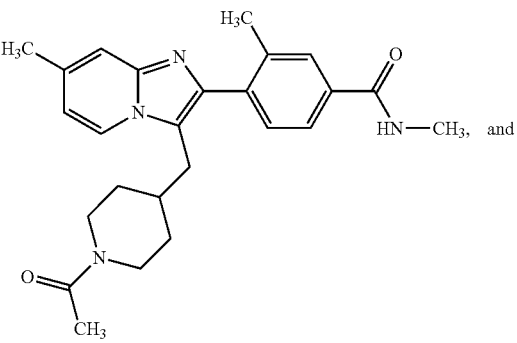
and

Compound 33

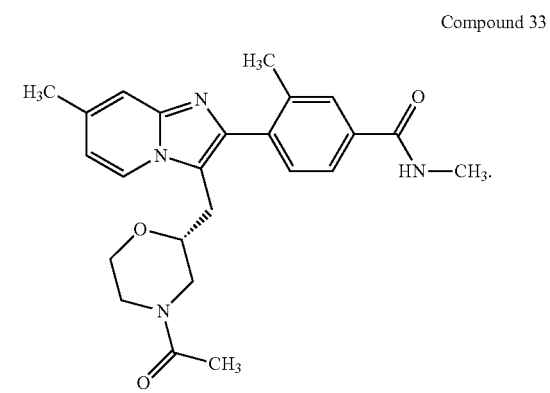 [SMILES: CNC(=O)c1cc(F)c(-c2nc3cc(C)ccn3c2C[C@H]2CN(C(=O)OC)CCO2)c(F)c1]

In some embodiments of the methods described herein, the selective P2X3 antagonist is a compound of Formula (I), or a pharmaceutically acceptable salt thereof, wherein the compound of Formula (I) corresponds in structure to (Compound 1)

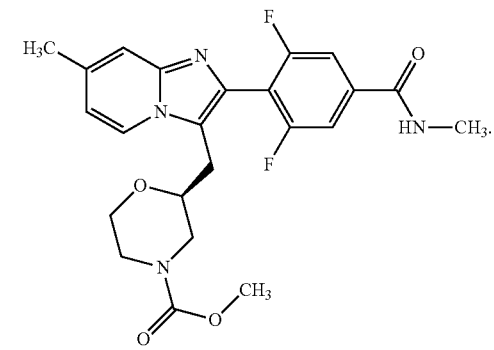

In some embodiments of the methods described herein, the selective P2X3 antagonist is a compound of Formula (I), or a pharmaceutically acceptable salt thereof, wherein the compound of Formula (I) corresponds in structure to (Compound 20)

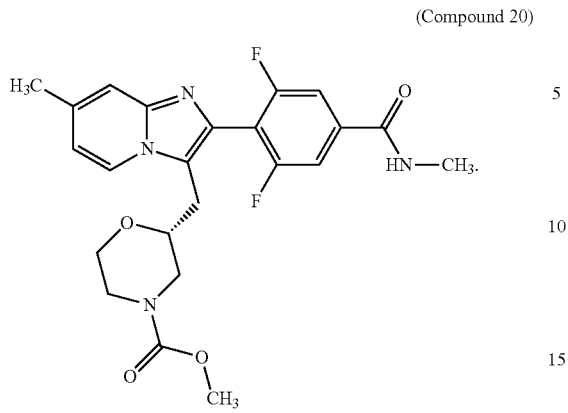

In some embodiments of the methods described herein, the selective P2X3 antagonist is a compound of Formula (I), or a pharmaceutically acceptable salt thereof, wherein the compound of Formula (I) corresponds in structure to (Compound 2)

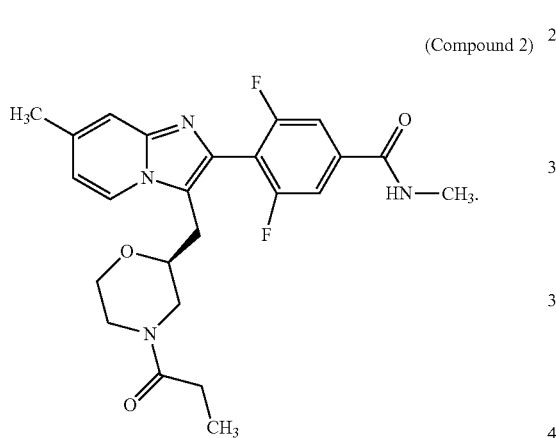

In some embodiments of the methods described herein, the selective P2X3 antagonist is a compound of Formula (I), or a pharmaceutically acceptable salt thereof, wherein the compound of Formula (I) corresponds in structure to (Compound 21)

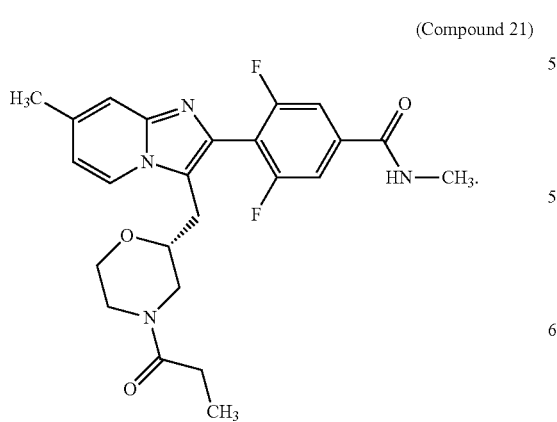

In some embodiments of the methods described herein, the selective P2X3 antagonist corresponds in structure to (Compound 34)

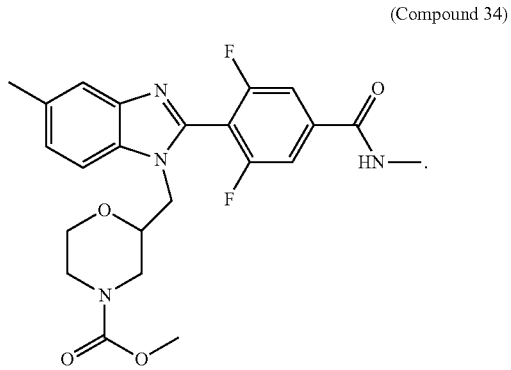

In some embodiments of the methods described herein, the selective P2X3 antagonist corresponds in structure to (Compound 35)

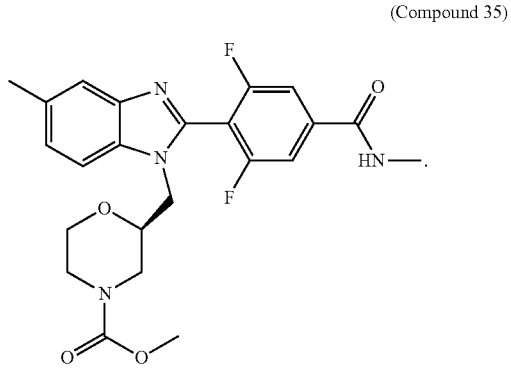

In some embodiments of the methods described herein, the selective P2X3 antagonist corresponds in structure to (Compound 36)

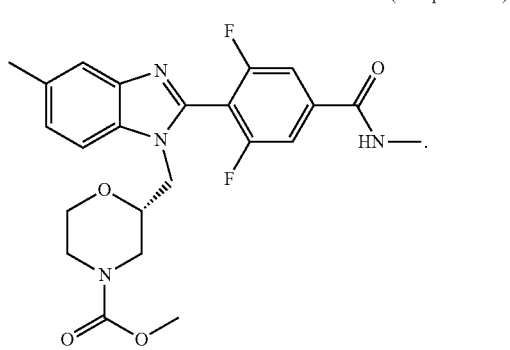

In some embodiments, is a method of avoiding loss of taste response while treating a chronic cough patient, the method comprising administering to the patient a therapeutically effective amount of a selective P2X3 antagonist, wherein the selective P2X3 antagonist is selective for P2X3 homomeric receptor antagonism versus P2X2/3 heteromeric receptor antagonism and is a compound of Formula (I) described herein, or a pharmaceutically acceptable salt thereof. In some embodiments, is a method of avoiding loss of taste response while treating a chronic cough patient, the method comprising administering to the patient a therapeutically effective amount of a selective P2X3 antagonist, wherein the selective P2X3 antagonist is at least 10-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 20-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 25-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 30-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 40-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 50-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 60-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 70-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 80-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 90-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 100-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 150-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 200-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 250-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 300-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 350-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 400-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 450-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 500-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 600-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 700-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 800-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 900-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 1000-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 1200-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 1400-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 1600-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 1800-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 2000-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 2200-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 2500-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 2700-fold selective for P2X3 homomeric receptor antagonism versus P2X2/3 heteromeric receptor antagonism and is a compound of Formula (I) described herein, or a pharmaceutically acceptable salt thereof. In some embodiments is a method of avoiding loss of taste response while treating a chronic cough patient, the method comprising administering to the patient a therapeutically effective amount of a selective P2X3 antagonist, wherein the selective P2X3 antagonist is at least 3000-fold selective for P2X3 homomeric receptor antagonism versus P2X2/3 heteromeric receptor antagonism and is a compound of Formula (I) described herein, or a pharmaceutically acceptable salt thereof.

In some embodiments of the methods described herein, the chronic cough is due or associated with asthma, chronic bronchitis, chronic postnasal drip, eosinophilic bronchitis, or chronic obstructive pulmonary disease.

In some embodiments of the methods described herein, the chronic cough is due or associated with chronic infections such as bronchiectasis, tuberculosis, or cystic fibrosis.

In some embodiments of the methods described herein, the chronic cough is due or associated with lung tumors such as bronchogenic carcinoma, alveolar cell carcinoma, benign airway tumors, or mediastinal tumors.

In some embodiments of the methods described herein, the chronic cough is due or associated with a cardiovascular disease such as left ventricular failure, pulmonary infarction, or aortic aneurysm.

In some embodiments of the methods described herein, the chronic cough is due or associated with reflux oesophagitis, recurrent aspiration, endobronchial sutures, postnasal drip syndrome, or rhinosinusitis.

In certain embodiments, a disclosed compound utilized by one or more of the foregoing methods is one of the generic, subgeneric, or specific compounds described herein, such as a compound of Formula (I) described herein.

Preparation of the Compounds

The compounds used in the methods described herein are made according to procedures disclosed in U.S. Pat. No. 9,598,409, which is herein incorporated by reference in its entirety, or by known organic synthesis techniques, starting from commercially available chemicals and/or from compounds described in the chemical literature. Commercially available chemicals are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^2$H, 3H, $^{13}$C, $^{14}$C, $^{15}$N, $^{18}$O, $^{17}$O, $^{31}$F, $^{32}$F, $^{35}$S, $^{18}$F, and $^{36}$Cl, respectively. Compounds described herein, and the pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., u isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

EXAMPLES

These examples are provided for illustrative purposes only and not to limit the scope of the claims provided herein.

Example 1: Potency and Selectivity for Human P2X3 and P2X2/3 Receptors

The ability of the compounds described herein and Gefapixant (also known as AF-219) to act as an antagonist of the P2X3 and P2X2/P2X3 channel (encoded by the human P2RX2 and P2RX3 genes, stably expressed in HEK293 cells) was evaluated with a Fluo-8 calcium kit. Compounds 1, 2, 9, 11, 15, and AF-219 were evaluated at twelve concentrations.

For the antagonist effect assessment, the cells were pre-incubated with Compounds 1, 2, 9, 11, 15, and AF-219 for 20 minutes, then stimulated with the P2X3 and P2X2/P2X3 agonist α,β-methyleneATP (meATP) at final concentrations of 3 μM and 30 μM. Four minutes fifty seconds after addition of meATP, ionomycin was added at a final concentration of 5 μM in order to obtain the maximum calcium influx and fluorescence signal possible from the cells. Fluorescence was recorded continuously for 10 minutes, starting 10 seconds prior to the addition of meATP. $IC_{50}$s obtained using the above methods are shown in FIG. 3. These results indicate that compounds of Formula I (compounds 1, 2, 9, 11, and 15) are selective P2X3 antagonists, while AF-219 is not.

Example 2: Guinea Pig Cough Response Model

The anti-tussive effect of Compound 1 was compared to that of AF-219 in a guinea pig cough model. Guinea pigs are the most commonly used animal in cough studies for both the investigation of the cough reflex at a fundamental level and for use as an antitussive screen (Mackensie et al., Drug Discovery Today, 2004, 1, 297-302). In the guinea pig, it was shown that exposure to ATP and histamine aerosols increases cough responses to tussive stimuli via P2X3 receptor-mediated mechanisms (Kamei et al., Eur J Pharmacol (2005) 528: 158-161; Kamei et al., Eur J Pharmacol (2006) 547: 160-164).

Figure 4:
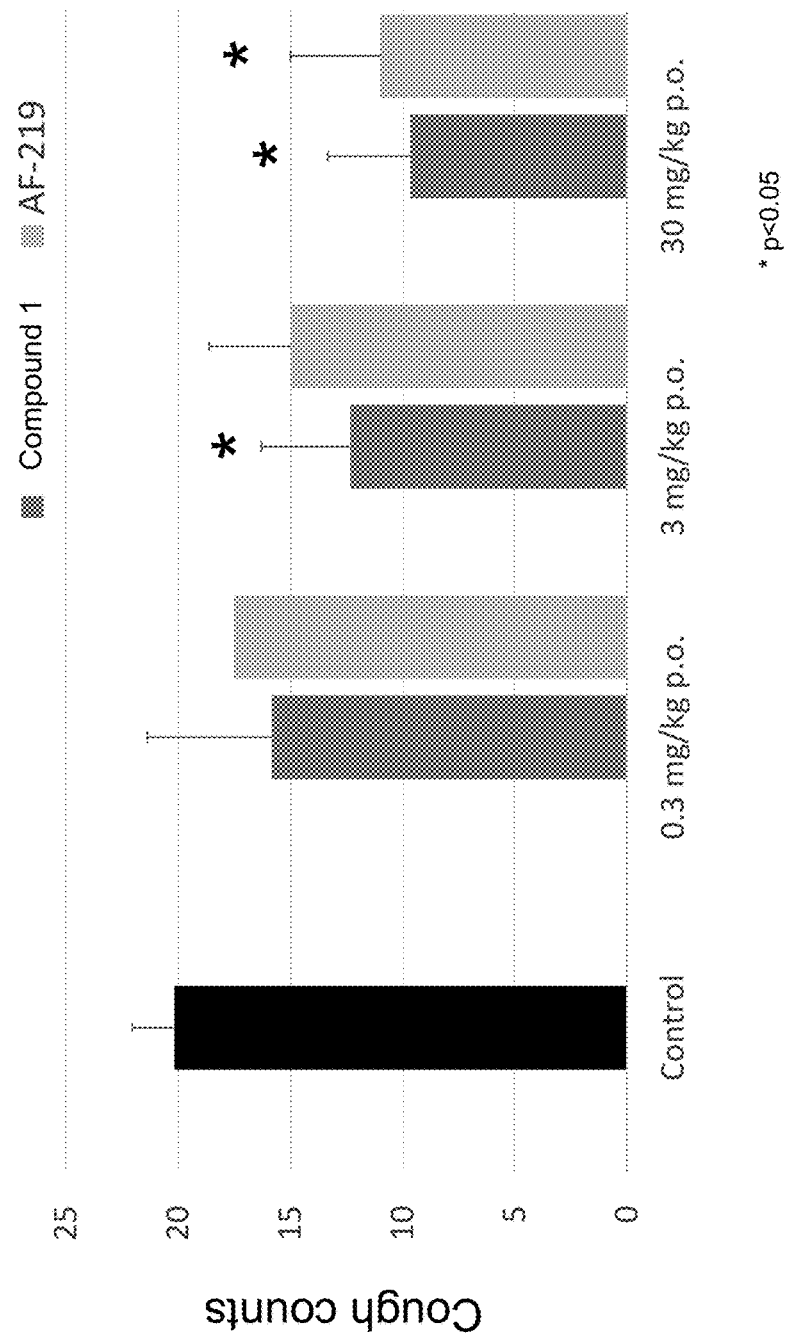
FIG. 4 shows the anti-tussive effect of Compound 1 and AF-219 at three doses in a guinea pig cough model.

Treatments (control, Compound 1 (0.3, 3 and 30 mg/kg) or AF-219 (0.3, 3 or 30 mg/kg)) were administered orally in seven groups of 6 animals 2 hours prior to tussive agent exposure (citric acid and histamine) and the number of coughs were counted for a period of 15 minutes. Both treatments showed comparable dose-dependent reduction in cough frequency as compared to the control. The reduction in cough was statistically significant at 3 mg/kg (39% vs. control) and 30 mg/kg (52% vs. control) with Compound 1, and at 30 mg/kg (45% vs. control) with AF-219 (FIG. 4).

Example 3: Time Course Study in Guinea Pig Cough Response Model

Using the same guinea pig cough model as described in Example 2, a time course study was conducted to assess the duration of the anti-tussive effect of Compound 1 and AF-219 following the administration of a single oral 30 mg/kg dose. In this study, animals in groups of 6 were exposed to tussive agents (citric acid and histamine) at various times after the administration of the study drugs (2, 4, 6, 8 and 12 hours post-dose for Compound 1; and 2 and 8 hours post-dose for AF-219) and the number of coughs were measured for 15 minutes. The reduction in cough frequency compared to control was shown to be statistically significant at 2, 4 and 6 hours post-dose with Compound 1, and at 2 hours post-dose with AF-219. The anti-tussive effect was no longer significant at 8 hours post-dose for both agents. These results indicate that Compound 1 and AF-219 have comparable duration of effect (FIG. 5).

Example 4: Two Bottle Taste Study

A rat taste model was used to compare the effect of Compound 1 on taste function with that of AF-219. Animals were water-fasted overnight and presented with one bottle of water and one bottle of (bitter-tasting) quinine at the time corresponding to the maximum plasma concentration of study drugs; and the volume of liquid consumed from each bottle was measured for 15 minutes. Treatments (control, Compound 1 (10 or 20 mg/kg) or AF-219 (10 or 20 mg/kg)) were administered intraperitoneally in two groups of 10 rats. Animals treated with Compound 1 did not drink more quinine than the control animals, while those treated with AF-219 drank significantly (approximately 5 times) more quinine than the control at the two doses tested. These results indicate that AF-219 altered taste function, while Compound 1 did not (FIG. 6).

We claim:

1. A method of avoiding loss of taste response while treating a chronic cough patient, the method comprising administering to the patient a therapeutically effective amount of a selective P2X3 antagonist, wherein the selective P2X3 antagonist is at least 10-fold selective for P2X3 homomeric receptor antagonism versus P2X2/3 heteromeric receptor antagonism, wherein the selective P2X3 antagonist is a compound of Formula (I), or a pharmaceutically acceptable salt thereof:

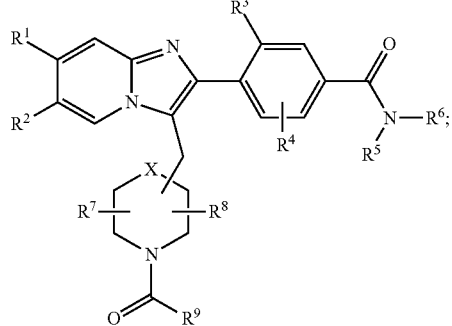

Formula (I)

wherein:

$R^1$ is selected from the group consisting of cyano, halogen, methyl, and ethyl;

$R^2$ is selected from the group consisting of hydrogen, halogen, methyl, and ethyl;

$R^3$ is selected from the group consisting of halogen, methyl, and ethyl;

$R^4$ is selected from the group consisting of hydrogen, halogen, methyl, ethyl, and methoxy;

$R^5$ and $R^6$ are independently selected from the group consisting of hydrogen, $C_1$-$C_6$-alkyl, and hydroxy-$C_1$-$C_6$-alkyl; or $R^5$ and $R^6$, together with the nitrogen to which they are both attached, form a 5- or 6-member heterocycloalkyl, wherein the heterocycloalkyl is optionally substituted with one or more substituents independently selected from the group consisting of halogen, hydroxyl, and $C_1$-$C_4$-alkyl;

$R^7$ and $R^8$ are independently selected from the group consisting of hydrogen and $C_1$-$C_4$-alkyl;

$R^9$ is selected from the group consisting of $C_1$-$C_6$-alkyl, $C_3$-$C_6$-cycloalkyl, $C_1$-$C_6$-alkyl-$C_3$-$C_6$-cycloalkyl, halo-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl; and X is selected from a bond, $CH_2$ and O.

2. The method of claim 1, wherein the selective P2X3 antagonist is at least 20-fold selective, at least 50-fold selective, at least 100-fold selective, at least 500-fold selective, at least 1000-fold selective, at least 2000-fold selective, or at least 2700-fold selective for P2X3 homomeric receptor antagonism versus P2X2/3 heteromeric receptor antagonism.

3. The method of claim 1, wherein $R^1$ is methyl.

4. The method of claim 3, wherein $R^2$ is hydrogen.

5. The method of claim 4, wherein $R^3$ is fluoro.

6. The method of claim 5, wherein $R^4$ is fluoro.

7. The method of claim 6, wherein X is O.

8. The method of claim 7, wherein the compound corresponds in structure to:

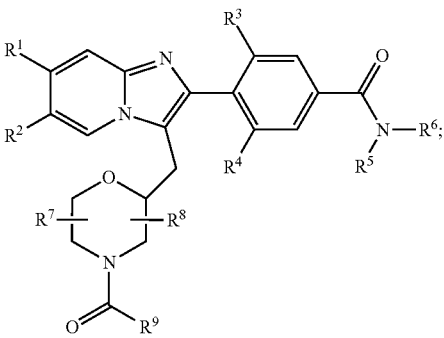

and $R^4$ is selected from the group consisting of halogen, methyl, and ethyl.

9. The method of claim 8, wherein $R^5$ is hydrogen.

10. The method of claim 9, wherein $R^6$ is $C_1$-$C_6$-alkyl.

11. The method of claim 10, wherein $R^6$ is methyl.

12. The method of claim 11, wherein $R^7$ is hydrogen and $R^8$ is hydrogen.

13. The method of claim 12, wherein $R^9$ is $C_1$-$C_6$-alkoxy.

14. The method of claim 13, wherein $R^9$ is methoxy.

15. The method of claim 1, wherein the compound corresponds in structure to:

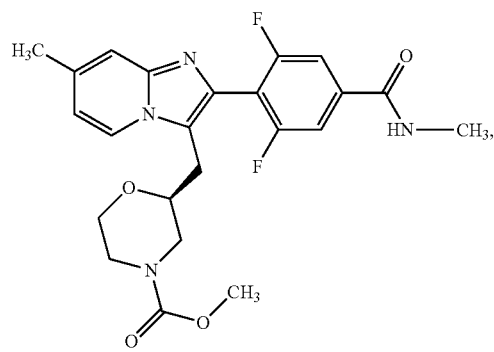

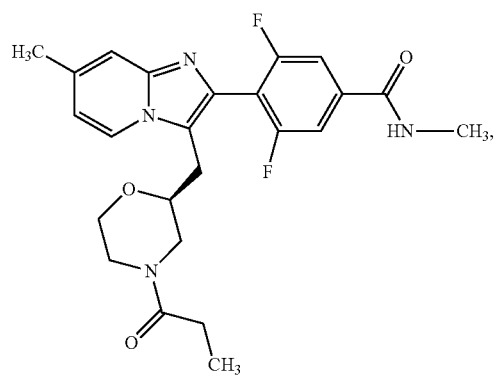

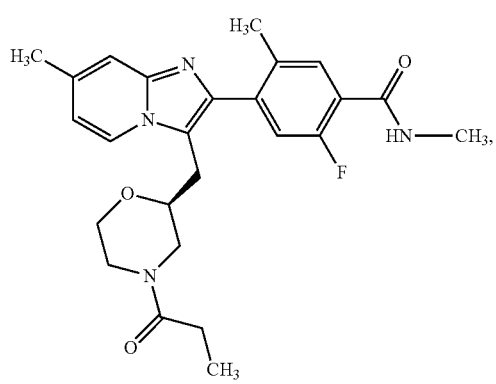
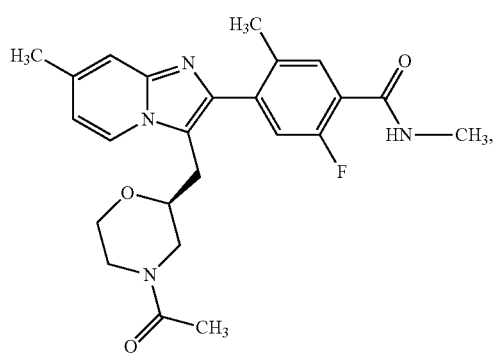
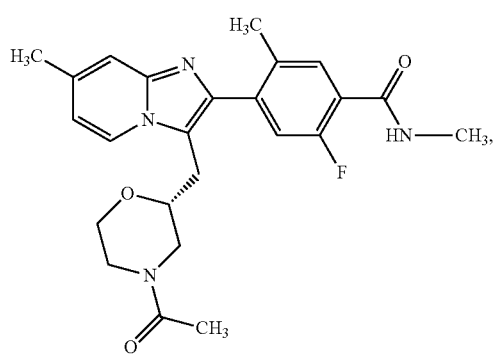
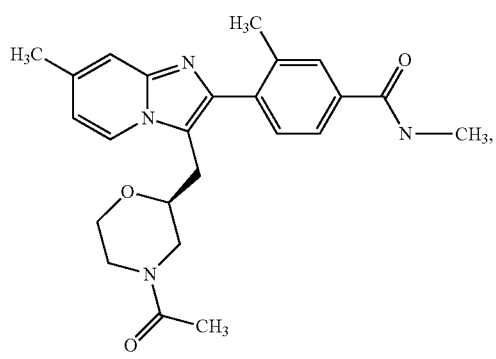
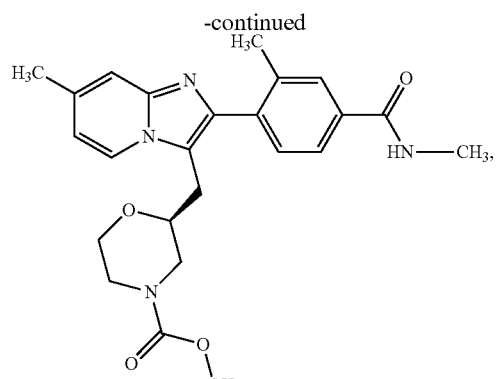
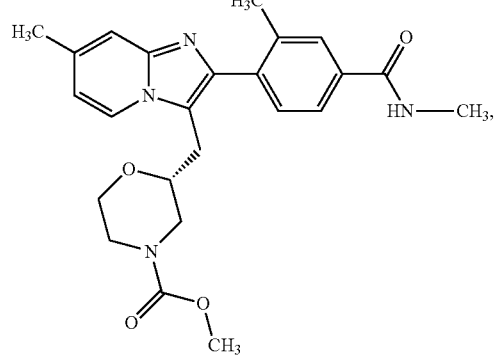
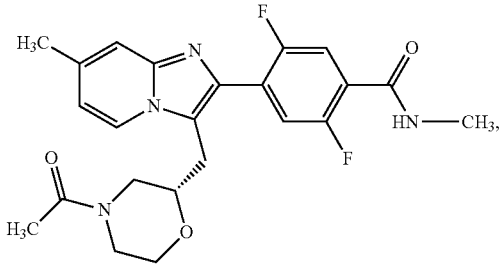
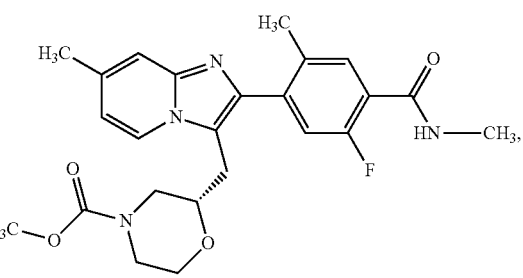
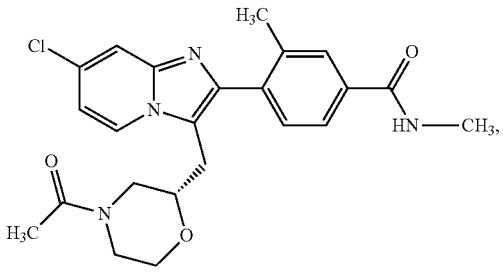

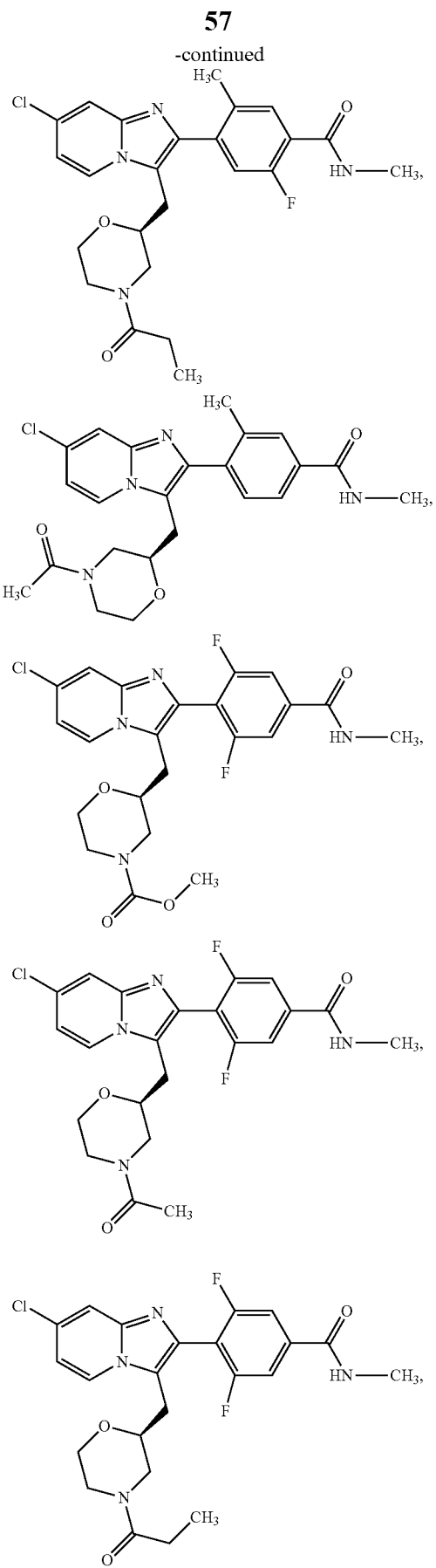
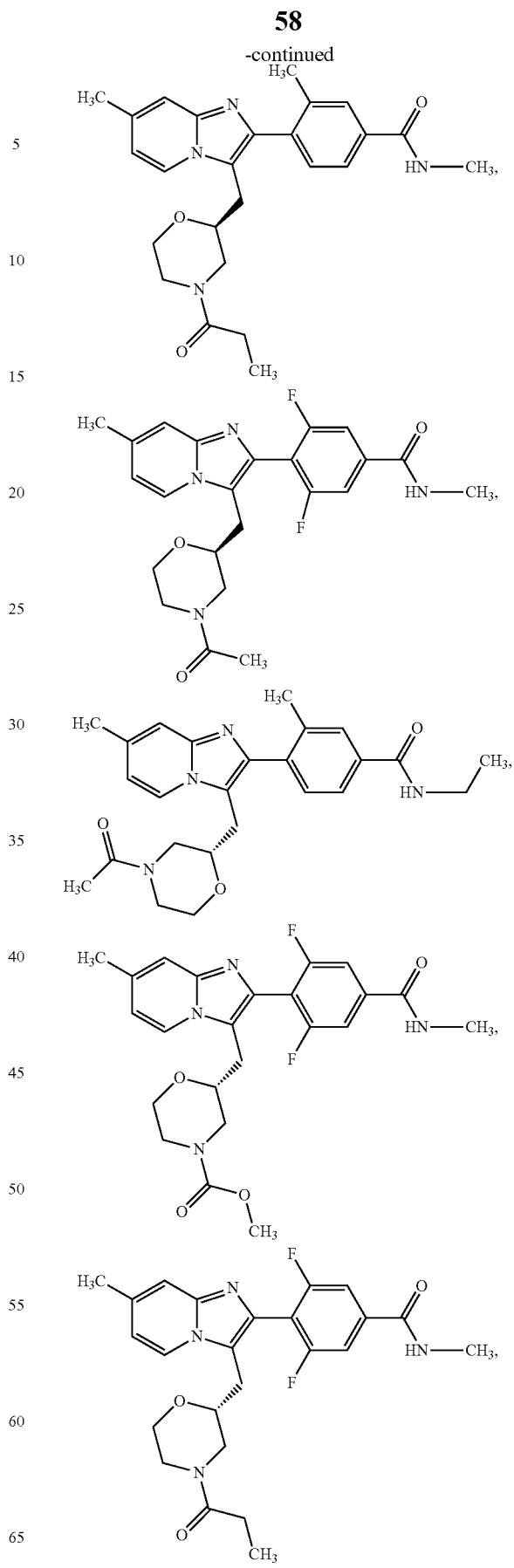

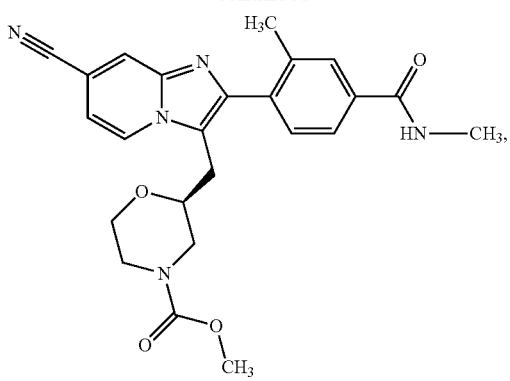
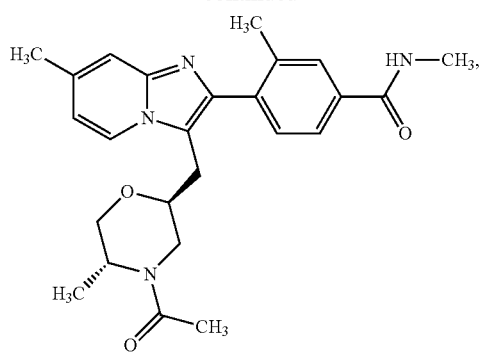
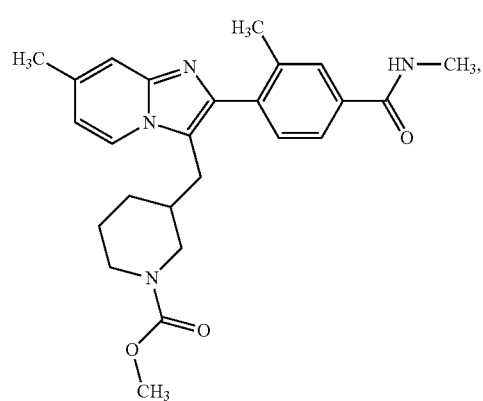
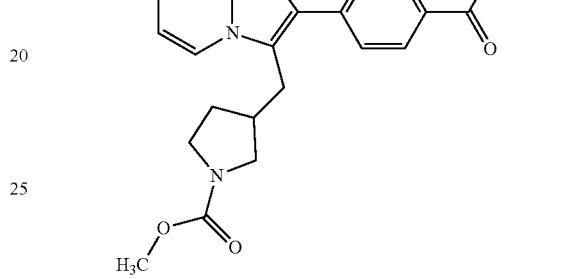
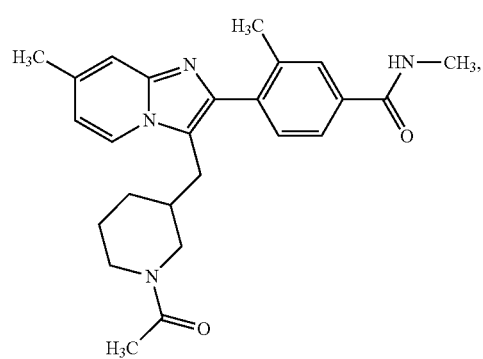
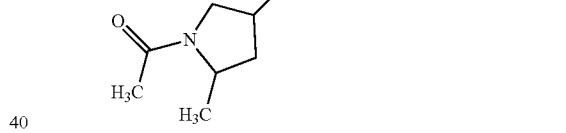
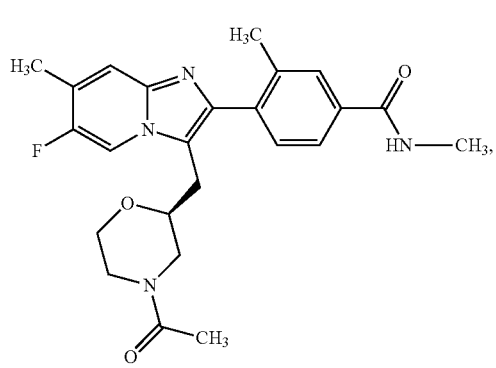
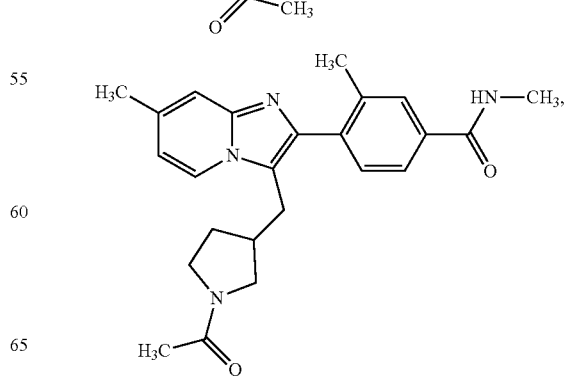

-continued
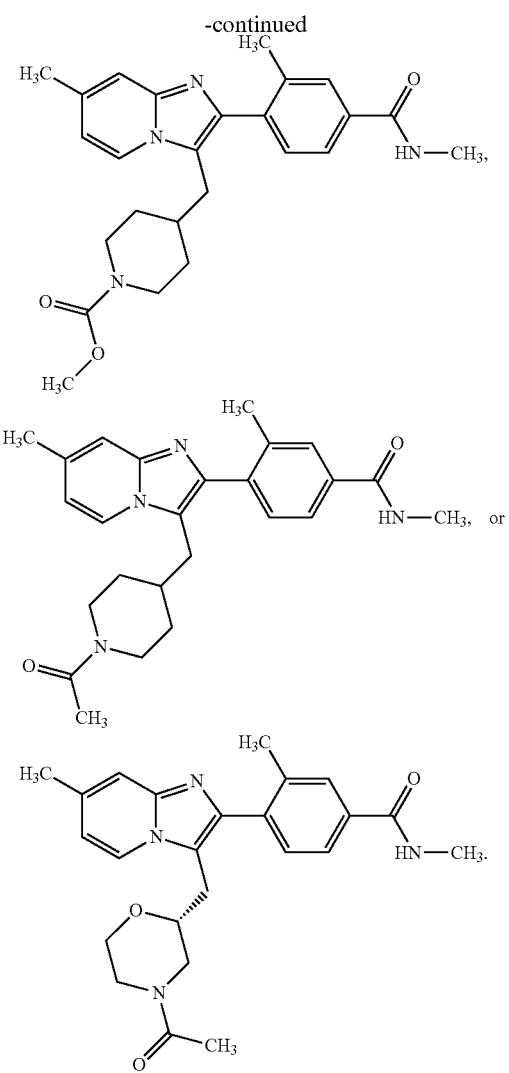
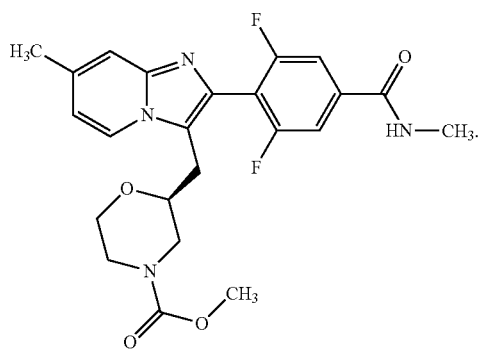 [SMILES: CNC(=O)c1cc(F)c(-c2nc3cc(C)ccn3c2C[C@H]2CN(C(=O)OC)CCO2)c(F)c1]
16. The method of claim 1, wherein the compound corresponds in structure to:
17. The method of claim 1, wherein the compound corresponds in structure to:
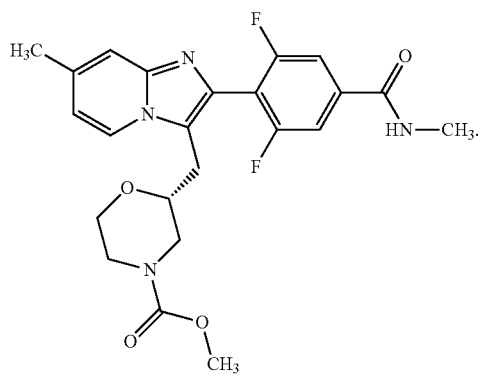 [SMILES: CNC(=O)c1cc(F)c(-c2nc3cc(C)ccn3c2C[C@@H]2CN(C(=O)OC)CCO2)c(F)c1]
18. The method of claim 1, wherein the compound corresponds in structure to:
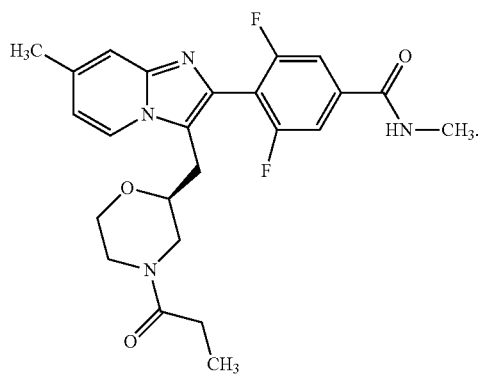 [SMILES: CCC(=O)N1CCO[C@@H](Cc2c(-c3c(F)cc(C(=O)NC)cc3F)nc3cc(C)ccn23)C1]
19. The method of claim 9, wherein the compound corresponds in structure to:
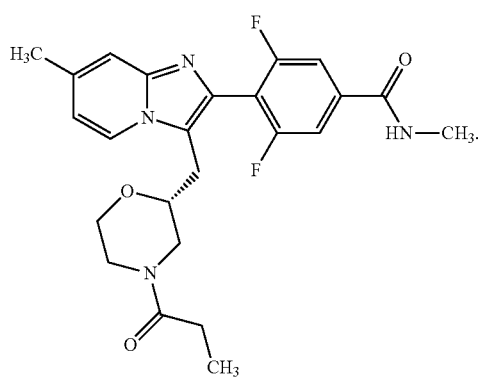 [SMILES: CCC(=O)N1CCO[C@H](Cc2c(-c3c(F)cc(C(=O)NC)cc3F)nc3cc(C)ccn23)C1]
* * * * *